US007709451B2

(12) United States Patent
Marshak-Rothstein et al.

(10) Patent No.: US 7,709,451 B2
(45) Date of Patent: May 4, 2010

(54) METHOD AND COMPOSITION FOR TREATING IMMUNE COMPLEX ASSOCIATED DISORDERS

(75) Inventors: Ann Marshak-Rothstein, Newton, MA (US); Elizabeth A. Leadbetter, Roslindale, MA (US); Ian R. Rifkin, Boston, MA (US); Mark J. Shlomchik, Woodbridge, CT (US)

(73) Assignees: Trustees of Boston University, Boston, MA (US); Yale University, New Haven, CT (US)

( * ) Notice: Subject to any disclaimer, the term of this patent is extended or adjusted under 35 U.S.C. 154(b) by 998 days.

(21) Appl. No.: 10/487,885

(22) PCT Filed: Sep. 9, 2002

(86) PCT No.: PCT/US02/28708

§ 371 (c)(1),
(2), (4) Date: Sep. 27, 2004

(87) PCT Pub. No.: WO03/022296

PCT Pub. Date: Mar. 20, 2003

(65) Prior Publication Data

US 2005/0106142 A1    May 19, 2005

Related U.S. Application Data

(60) Provisional application No. 60/318,096, filed on Sep. 7, 2001, provisional application No. 60/067,578, filed on Sep. 19, 1997.

(51) Int. Cl.
*A61K 31/52* (2006.01)
*A61K 31/04* (2006.01)

(52) U.S. Cl. .................... 514/44; 424/144.1
(58) Field of Classification Search .................. None
See application file for complete search history.

(56) References Cited

U.S. PATENT DOCUMENTS

| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |
| 6,239,116 | B1 | 5/2001 | Krieg et al. |
| 6,339,068 | B1 | 1/2002 | Krieg et al. |
| 6,406,705 | B1 | 6/2002 | Davis et al. |
| 6,429,199 | B1 | 8/2002 | Krieg et al. |
| 6,653,292 | B1 | 11/2003 | Krieg et al. |
| 2002/0077304 | A1 | 6/2002 | Persing et al. |
| 2004/0023870 | A1 | 2/2004 | Dedera et al. |

FOREIGN PATENT DOCUMENTS

| WO | WO 98/18810 A1 | 5/1998 |
| WO | WO 99/01154 A1 | 1/1999 |
| WO | WO 01/22972 A2 | 4/2001 |
| WO | WO 01/36488 A1 | 5/2001 |
| WO | WO 01/55386 A1 | 8/2001 |
| WO | WO 01/97843 A2 | 12/2001 |
| WO | WO 02/051430 A2 | 7/2002 |
| WO | WO 03/035695 A2 | 5/2003 |

OTHER PUBLICATIONS

Liew et al Nature Reviews Immunology, vol. 5, Jun. 2005, pp. 446-458.*
Akira et al., Toll-like receptors: critical proteins linking innate and acquired immunity. Nat Immunol. Aug. 2001;2(8):675-80.
Alexopoulou, Recognition of double-stranded RNA and activation of NF-kappaB by Toll-like receptor 3. Nature. Oct. 18, 2001;413(6857):732-8.
Ballas et al., Divergent therapeutic and immunologic effects of oligodeoxynucleotides with distinct CpG motifs. J Immunol. Nov. 1, 2001;167(9):4878-86.
Banchereau et al., Immunobiology of dendritic cells. Annu Rev Immunol. 2000;18:767-811.
Bell et al., Immunogenic DNA-related factors. Nucleosomes spontaneously released from normal murine lymphoid cells stimulate proliferation and immunoglobulin synthesis of normal mouse lymphocytes. J Clin Invest. May 1990;85(5):1487-96.
Bell et al., The spontaneous apoptotic cell death of normal human lymphocytes in vitro: the release of, and immunoproliferative response to, nucleosomes in vitro. Clin Immunol Immunopathol. Jul. 1991;60(1):13-26.
Chaudhary et al., Cloning and characterization of two Toll/Interleukin-1 receptor-like genes TIL3 and TIL4: evidence for a multi-gene receptor family in humans. Blood. Jun. 1, 1998;91(11):4020-7.

(Continued)

*Primary Examiner*—Bridget E Bunner
*Assistant Examiner*—Fozia M Hamud
(74) *Attorney, Agent, or Firm*—Wolf, Greenfield & Sacks, P.C.

(57) ABSTRACT

The present invention provides methods and compositions for treating immune complex associated diseases (ICAD), such as SLE, rheumatoid arthritis, and hepatitis-C related immune complex disease (e.g., cryoglobulinemia) in a subject having an ICAD or at risk for developing ICAD. The invention is based upon the surprising finding that chromatin-containing immune complexes activate autoreactive B cells and dendritic cells by a dual receptor engagement process which, in both cell types, involves a Toll-like receptor (TLR). The methods of treating ICAD comprise administering a compound to an individual in need thereof that either 1) inhibits formation of the immune complex either by preventing formation and/or binding to the TLR, or 2) interferes with binding of an autoantigen-containing immune complex (or the antigenic component thereof) to the TLR, or 3) inhibits signaling pathways initiated by dual engagement of BCR and TLR (in B cells) or FcR and TLR (in dendritic cells) via immune complexed or uncomplexed autoantigens.

2 Claims, 12 Drawing Sheets

OTHER PUBLICATIONS

Chuang et al., Cloning and characterization of a sub-family of human toll-like receptors: hTLR7, hTLR8 and hTLR9. Eur Cytokine Netw. Sep. 2000;11(3):372-8.

Du et al., Three novel mammalian toll-like receptors: gene structure, expression, and evolution. Eur Cytokine Netw. Sep. 2000;11(3):362-71.

Häcker et al., CpG-DNA-specific activation of antigen-presenting cells requires stress kinase activity and is preceded by non-specific endocytosis and endosomal maturation. EMBO J. Nov. 2, 1998;17(21:6230-40.

Hemmi et al., A Toll-like receptor recognizes bacterial DNA. Nature. Dec. 7, 2000;408(6813):740-5. Erratum in: Nature Feb. 1, 2001;409(6820):646.

Jakob et al., Activation of cutaneous dendritic cells by CpG-containing oligodeoxynucleotides: a role for dendritic cells in the augmentation of Th1 responses by immunostimulatory DNA. J Immunol. Sep. 15, 1998;161(6):3042-9.

Leadbetter et al., Chromatin-IgG complexes activate B cells by dual engagement of IgM and Toll-like receptors. Nature. Apr. 11, 2002;416(6881):603-7.

Leadbetter et al., Toll-like receptors and activation of autoreactive B cells. Curr Dir Autoimmun. 2003;6:105-22.

Lenert et al., CpG stimulation of primary mouse B cells is blocked by inhibitory oligodeoxyribonucleotides at a site proximal to NF-kappaB activation. Antisense Nucleic Acid Drug Dev. Aug. 2001;11(4):247-56.

Li et al., An essential role of the NF-kappa B/Toll-like receptor pathway in induction of inflammatory and tissue-repair gene expression by necrotic cells. J Immunol. Jun. 15, 2001;166(12):7128-35.

Lipford et al., CpG-DNA-mediated transient lymphadenopathy is associated with a state of Th1 predisposition to antigen-driven responses. J Immunol. Aug. 1, 2000;165(3):1228-35.

Mackay et al., BAFF: a fundamental survival factor for B cells. Nat Rev Immunol. Jul. 2002;2(7):465-75.

Matsumoto et al., Establishment of a monoclonal antibody against human Toll-like receptor 3 that blocks double-stranded RNA-mediated signaling. Biochem Biophys Res Commun. May 24, 2002;293(5):1364-9.

Medzhitov et al., A human homologue of the Drosophila Toll protein signals activation of adaptive immunity. Nature. Jul. 24, 1997;388(6640):394-7.

Monestier et al., Specificities and genetic characteristics of nucleosome-reactive antibodies from autoimmune mice. Mol Immunol. Jan. 1996;33(1):89-99.

Muzio et al., Irak (Pelle) family member IRAK-2 and MyD88 as proximal mediators of IL-1 signaling. Science. Nov 28, 1997;278(5343):1612-5.

Pike et al., Culture in liquid medium of single, hapten-specific, antibody-producing B lymphocytes. Methods Enzymol. 1987;150:265-75.

Rifkin et al., Immune complexes present in the sera of autoimmune mice activate rheumatoid factor B cells. J Immunol. Aug. 1, 2000;165(3):1626-33.

Rock et al., A family of human receptors structurally related to Drosophila Toll. Proc Natl Acad Sci U S A. Jan. 20, 1998;95(2):588-93.

Shlomchik et al., From T to B and back again: positive feedback in systemic autoimmune disease. Nat Rev Immunol. Nov. 2001;1(2):147-53.

Tan et al., Antinuclear antibodies: diagnostic markers for autoimmune diseases and probes for cell biology. Adv Immunol. 1989;44:93-151.

Viglianti GA et al., Activation of autoreactive B cells by CpG dsDNA. Immunity. Dec. 2003;19(6):837-47.

Wang et al., Autoantigen-specific B cell activation in Fas-deficient rheumatoid factor immunoglobulin transgenic mice. J Exp Med. Sep. 6, 1999;190(5):639-49.

Wesche et al., MyD88: an adapter that recruits IRAK to the IL-1 receptor complex. Immunity. Dec. 1997;7(6):837-47.

Yi et al., CpG motifs in bacterial DNA activate leukocytes through the pH-dependent generation of reactive oxygen species. J Immunol. May 15, 1998;160(10):4755-61.

Boule, M. et al., Toll-like receptor 9-dependent and -independent dendritic cell activation by chromatin-immunoglobulin G complexes. J Exp Med. Jun. 21, 2004;199(12):1631-40.

Bykerk, V. et al., A Randomized Study of The Effect of Withdrawing Hydroxychloroquine Sulfate in Systemic Lupus Erythematosus, N.E. Journ. Med. Jan. 17, 1991 324 (3):150-154.

Furst, D. et al., Dose-loading with hydroxychloroquine improves the rate of response in early, active rheumatoid arthritis: a randomized, double-blind six-week trial with eighteen-week extension. Arthritis Rheum. Feb. 1999;42(2):357-65.

Krieg, A. et al., A role for Toll in autoimmunity. Nat Immunol. May 2002;3(5):423-4.

Rifkin, I. et al., Toll-like receptors, endogenous ligands, and systemic autoimmune disease. Immunol Rev. 2005 Apr. 2005;204:27-42.

Stunz, L. et al., Inhibitory oligonucleotides specifically block effects of stimulatory CpG oligonucleotides in B cells. Eur J Immunol. May 2002;32(5):1212-22.

Vinuesa CG et al., DNA drives autoimmunity. Nature. Apr. 11, 2002;416(6881):595-8.

Yi Ak et al., CpG DNA rescues B cells from apoptosis by activating NFkappaB and preventing mitochondrial membrane potential disruption via a chloroquine-sensitive pathway. *Int Immunol.* Dec. 1999;11(12):2015-24.

* cited by examiner

SEQUENCE LISTING

<160> NUMBER OF SEQ ID NOS: 3

<210> SEQ ID NO 1
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 1
tggcatgcct ccatcatagt taacc                                    25

<210> SEQ ID NO 2
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 2
gtcagaaaca accaccacca tgc                                      23

<210> SEQ ID NO 3
<211> LENGTH: 25
<212> TYPE: DNA
<213> ORGANISM: Artificial sequence -continued

```
<220> FEATURE:
<223> OTHER INFORMATION: synthetic oligonucleotide

<400> SEQUENCE: 3
atcgccttct atcgccttct tgacg                                              25
```

METHOD AND COMPOSITION FOR TREATING IMMUNE COMPLEX ASSOCIATED DISORDERS

This invention was made with Government Support under Contract Nos. R01 AR-35230 and K08 DK-02597 awarded by the National Institutes of Health. The Government has certain rights in the invention.

BACKGROUND OF THE INVENTION

1. Field of the Invention

The present invention relates to methods and compositions for treating immune complex associated diseases, preferably systemic lupus erythematosus (SLE), and other systemic autoimmune diseases associated with the subject having aberrant Toll-like receptor (TLR)/B cell receptor (BCR) dual engagement (in B cells) or TLR/Fc gamma receptor dual engagement (in dendritic cells and/or macrophages).

2. Background

Autoimmune diseases are a fairly common but poorly understood group of diseases in which an individual's immune system either 1) begins recognizing self antigens as foreign and starts destroying tissues expressing such antigens thereby causing a disease, or 2) forms immune complexes with these antigens which then deposit in tissues and cause inflammatory pathology. Such autoimmune diseases include, for example, diabetes wherein the immune system turns against and destroys insulin producing pancreatic islet cells; multiple sclerosis, wherein the target antigen is the myelin sheath protecting neurons leading to destruction of function of motorneurons; psoriasis, where the target of the immune system is skin; rheumatoid arthritis, where the target organ is cartilage; and systemic lupus erythematosus (SLE), which presents itself as targeting a variety of tissues with no apparent specificity or selectivity although the target antigens themselves are extremely consistent and characteristic. Because the mechanisms leading to the development of autoimmune diseases in general are mostly unknown, their treatment is often directed to generally suppressing the immune system. Such general immunosuppressive therapies often cause a variety of undesirable side effects including cancer, infertility, and increased susceptibility to infections by viruses, fungi, yeast, and bacteria Therefore, it would be desirable to understand the mechanisms that cause the immune system to turn against self antigens to enable development of more specific therapies for the treatment of the autoimmune diseases.

An example of a poorly understood autoimmune disease is systemic lupus erythematosus (SLE), commonly known as Lupus. SLE is characterized by dysregulation of the immune system resulting in the production of antinuclear antibodies, the generation of circulating immune complexes, and the activation of the complement system. The immune complexes build up in the tissues and joints causing inflammation, and degradation to both joints and tissues. While the word "systemic" correctly suggests that the disease affects the entire body and most organ systems, the disease most often involves inflammation and consequent injury to the joints, skin, kidney, brain, the membranes in body cavities, lung, heart, and gastrointestinal tract. An individual with SLE often experiences unpredictable acute episodes or "outbreaks" and equally unexpected remissions. The pathologic hallmark of the disease is recurrent, widespread, and diverse vascular lesions resembling a rash or changes on the surface of the skin.

The prevalence of SLE in the United States is an issue of some debate. Estimates of prevalence range from 250,000 to 2,000,000 persons. Although reported in both the extremely old and the extremely young, the disease mainly affects women of childbearing age. Among children SLE is three times more common in females than in males. In the 60% of SLE patients who experience the onset of this disease between puberty and the fourth decade of life, the female to male ratio is 9:1. Thereafter, the female preponderance again falls to that observed in prepubescent children (i.e. 3:1). In addition, the disorder appears to be three times more common in persons of African and Asian descent than in persons of Caucasian descent.

The etiology of SLE remains unknown. A genetic predisposition, the systemic proliferation of sex hormones, and various environmental triggers, such as viral infections have been suggested to play a role in triggering the aberrant immune responses that typify the disease. A role for genetics is suggested by the increased percentage of two histocompatibility antigens, HLA-DR2 and HLA-DR3, in patients with SLE. In addition, there is an increased frequency of the extended haplotypes HLA-A1, B8, and DR3 in affected individuals. The role of heredity is further supported by the concordance for this illness among monozygotic twins. The polygenic nature, however, of this genetic predisposition as well as the contribution of environmental factors is suggested by the concordance rate, which is only moderate and reported to be between 25% and 60%.

The precise initiating etiology of SLE is unknown. However, it is generally accepted that most of the clinical manifestations of the disease are caused either directly or indirectly by autoantibody production and the subsequent formation of pathogenic immune complexes. These autoantibodies, which are produced by dysregulated B lymphocytes, have distinct specificities recognizing discrete nuclear autoantigens including, among others, DNA, nucleosomes and subnucleosomes. Certain RNA/protein complexes including the Sm antigen and small nuclear ribonucleoproteins (snRNP) are additional characteristic autoantigenic specificities. The pathogenic immune complexes are formed by binding of the autoantibodies to their respective nuclear autoantigens.

Autoantibodies in SLE often circulate as immune complexes (IC) bound with their respective autoantigens. Chromatin or chromatin fragments such as DNA, nucleosomes or subnucleosome particles are especially common autoantigenic specificities in both mice and humans (Tan, E. *Adv. Immunol.* 44, 93-151 (1989); Monestier and Novick, Mol. Immunol. 33: 89-99., 1996)

The central goals in the treatment of SLE, therefore, are either to attempt to suppress the dysfunctional B lymphocytes thereby decreasing the production of autoantibody or, to attempt to diminish the pathogenicity of the immune complexes once they have formed. At present these goals can only be achieved, and often incompletely so, by the use of intensive systemic immunosuppressive drug therapy using drugs such as cortisone, azathioprine, hydroxychloroquine and cyclophosphamide. These therapies are associated with many serious and undesirable side-effects including infections, infertility, retinopathy and cancer. Therefore, new treatments for SLE, and other autoimmune diseases, would be desirable.

SUMMARY OF THE INVENTION

It is therefore the purpose of the present invention to provide methods and compositions for treating immune complex associated diseases (ICAD), such as SLE, rheumatoid arthritis, and hepatitis-C related immune complex disease (e.g., cryoglobulinemia) in a subject having an ICAD or at risk for developing ICAD.

We have discovered that chromatin-containing immune complexes activate autoreactive B cells and dendritic cells by a dual receptor engagement process. In both cell types a Toll-like receptor (TLR) is involved. TLR9, located in a cytoplasmic compartment, is the essential second receptor required for cell activation. In the case of the B cell, the B cell antigen receptor located on the cell surface is the essential first receptor required for cell activation. In the case of the dendritic cell, a stimulatory Fc gamma receptor located on the cell surface is the essential first receptor required for cell activation. We have found a method of treating ICAD by administering a compound to an individual in need thereof that either 1) inhibits formation of the immune complex (i.e., autoantibody and nuclear autoantigen) either by preventing formation and/or binding to the Toll-like receptor (TLR), or 2) interferes with binding of an autoantigen-containing immune complex (or the antigenic component thereof) to the TLR, or 3) inhibits signaling pathways initiated by dual engagement of BCR and TLR (in B cells) or FcR and TLR (in dendritic cells) via immune complexed or uncomplexed autoantigens. The compound is administered in a pharmaceutically acceptable carrier.

Preferably, the ICAD is SLE, rheumatoid arthritis or hepatitis-C related immune complex disease (e.g., cryoglobulinemia). In an other embodiment, the ICAD is related to an immune reaction in a host after organ transplantation.

Although not working to be bound by theory, we believe that immune complexes (IC) containing an autoantigen, such as chromatin, but not IC containing a foreign antigen, are able to activate autoreactive B cells and that this activation is absolutely dependent on the ability of the autoantigen-containing IC to sequentially engage either the B cell receptor (BCR) in B cells or FcγR in dendritic cells, and a second receptor, a Toll-like receptor. This finding establishes a novel link between the innate and adaptive immune systems and suggests a general mechanism whereby autoreactive B cells or dendritic cells specific for protein/nucleic acid autoantigens are activated.

According to one aspect of the invention a method is provided for treating a patient having an ICAD or at risk for an ICAD by identifying an individual with ICAD and administering an effective amount of a compound capable of inhibiting the autoantigen or autoantigen/immune complex from forming and/or from activating B cells or dendritic cells.

A person at risk for ICAD or systemic autoimmune disease includes individuals having at least a parent, grandparent or sibling who has an ICAD or systemic autoimmune disease.

The compound is selected from a group consisting of compounds that bind components of the immune complex and either prevent its formation or prevent the autoantigen from activating a Toll-like receptor (TLR). Such compounds include Toll-like receptor decoys, compounds that inhibit the activity of MyD88, compounds that inhibit production of immune complex components (e.g., antisense nucleotides), dominant-negative TLR, a Toll-like receptor antagonist, and compounds that inhibit signaling pathways activated by the interaction or binding of the immune complex or autoantigen to the TLR. Preferably, the compound binds and/or inhibits function of Toll-like receptors TLR2, TLR3, and TLR9 or functional domains thereof. More preferably, the TLR is TLR3 or TLR9 or a functional fragment thereof.

Compounds that bind components of the immune complex and prevent its formation or prevent binding of the complex to the Toll-like receptor and compounds that inhibit MyD88 signaling include polyclonal and monoclonal antibodies, dominant negative proteins that can block wildtype TLR activity or block components of the TLR-mediated signaling cascade, inhibitory oligodeoxynucleotides (ODN), such as S-ODN 2088 (Lenart, et al., *Antisense Nucleic Acid Drug Dev.* 4, 247-256 (2001)), antisense nucleotides including RNA and modified nucleotides, or other pathway specific kinase inhibitors. The compound is a compound other than chloroquine.

In one embodiment the invention provides methods for screening compounds or agents that inhibit immune complex formation or binding to the Toll-like receptor and/or inhibit B cell/dendritic cell activation. The methods comprise contacting immune complex components with a test agent and measuring B cell or dendritic cell activation and/or proliferation and/or binding of the complex to the Toll-like receptor.

In an other embodiment, a method of diagnosing an ICAD is provided. The method comprises taking a biological sample comprising IgG of an individual suspected of having ICAD, incubating the biological sample together with RF+ B cells or dendritic cells, and measuring the activation of the RF+ B cells or dendritic cells, wherein a change in activity in the RF+ B cell or dendritic cell cultures exposed to the biological sample from the individual suspected of having ICAD relative to the RF+ B cells or dendritic cells exposed to a biological sample comprising IgG from a control individual is indicative of ICAD. Preferably, the change is an increase in activity. Activation of the B cells can be measured, for example by measuring proliferation or upregulation of co-stimulatory molecules such as CD80 and CD86 as well as upregulation of MHC class II molecules. Activation of dendritic cells can be assessed by measuring the expression of co-stimulatory molecules, production of cytokines, e.g., TNF-α, or changes in the dendritic cell phenotype.

In yet another embodiment, the invention provides an in vivo model system for evaluating a compound or an agent for its efficacy in treating ICAD. The model system comprises administering a test agent to an ICAD model animal including mouse and rat models, and measuring B cell or dendritic cell activation and/or proliferation and/or binding of the complex to the Toll-like receptor in such animal, wherein decreased activation is indicative of an agent which is capable of treating ICAD. Alternatively, one can use cell lines expressing Toll-like receptors and screen for compounds that modulate, preferably inhibit or block, such receptors.

Other aspects of the invention are disclosed infra.

BRIEF DESCRIPTION OF THE DRAWINGS

The accompanying drawings, which are incorporated in and constitute a part of this specification, illustrate embodiments of the invention and, together with the description, serve to explain and illustrate the objects, advantages, and principles of the invention. In the drawings.

In FIG. 2A, IC formation was confirmed by a shift in C1q binding activity relative to uncomplexed antibodies (down-triangle). In FIG. 2B the ability of the anti-TNP/TNP-BSA IC described above to stimulate RF+ B cell proliferation was compared to the stimulation induced by the anti-nucleosome mAb PR1-3, uncomplexed Hy1.2, C4010, or 50 µg/ml TNP-BSA.

In FIG. 4A, T-depleted spleen cells from wildtype (WT) and RF+ MyD88−/− mice were stained with B220 and an idiotype specific antibody, 4G7. In FIG. 4B, MyD88 WT or knock-out mice were identified by PCR. In FIG. 4C spleen cells from each of two WT (gray), RF+ MyD88+/+ (white), RF+ MyD88−/− (hatched) mice were stimulated with anti-IgM F(ab')$_2$, CpG S-ODN 1826, LPS, anti-nucleosome mAbs PR1-3, PL2-3, PL2-8, or 3% lpr/gld serum. Total cpm for the anti-IgM stimulated cultures were 83,414/39,049 (WT); 93,126/61,315 (RF+ MyD88+/+); and 39,826/57,484 (RF+ MyD88−/−). Results are expressed as the percentage of the anti-IgM response and are representative of four separate experiments.

In FIG. 5A, RF+ B cells were preincubated for 15 minutes with 1 or 2 µg/ml chloroquine (a), preincubated for 2 hrs with concanamycin B (b), or preincubated for 30 minutes with inhibitory CpG S-ODN 2088 (c), prior to the addition of the stimulatory ligands anti-IgM F (ab')$_2$, 5-50 µg/ml PL2-3, 0.3-2.0 µg/ml CpG S-ODN 1826, LPS, lipopeptide, or porin B. In FIG. 5B, RF+ B cells were preincubated for 30 min with 12 µg/ml CpG S-ODN 2088 prior to the addition of stimulatory ligands. Results are expressed as a percentage of the anti-IgM response in the absence of inhibitor. The data in (FIG. 5A) and (FIG. 5C) is representative of 2-4 experiments, while (FIG. 5B) is the mean of two experiments.

DETAILED DESCRIPTION OF THE INVENTION

Figure 1:
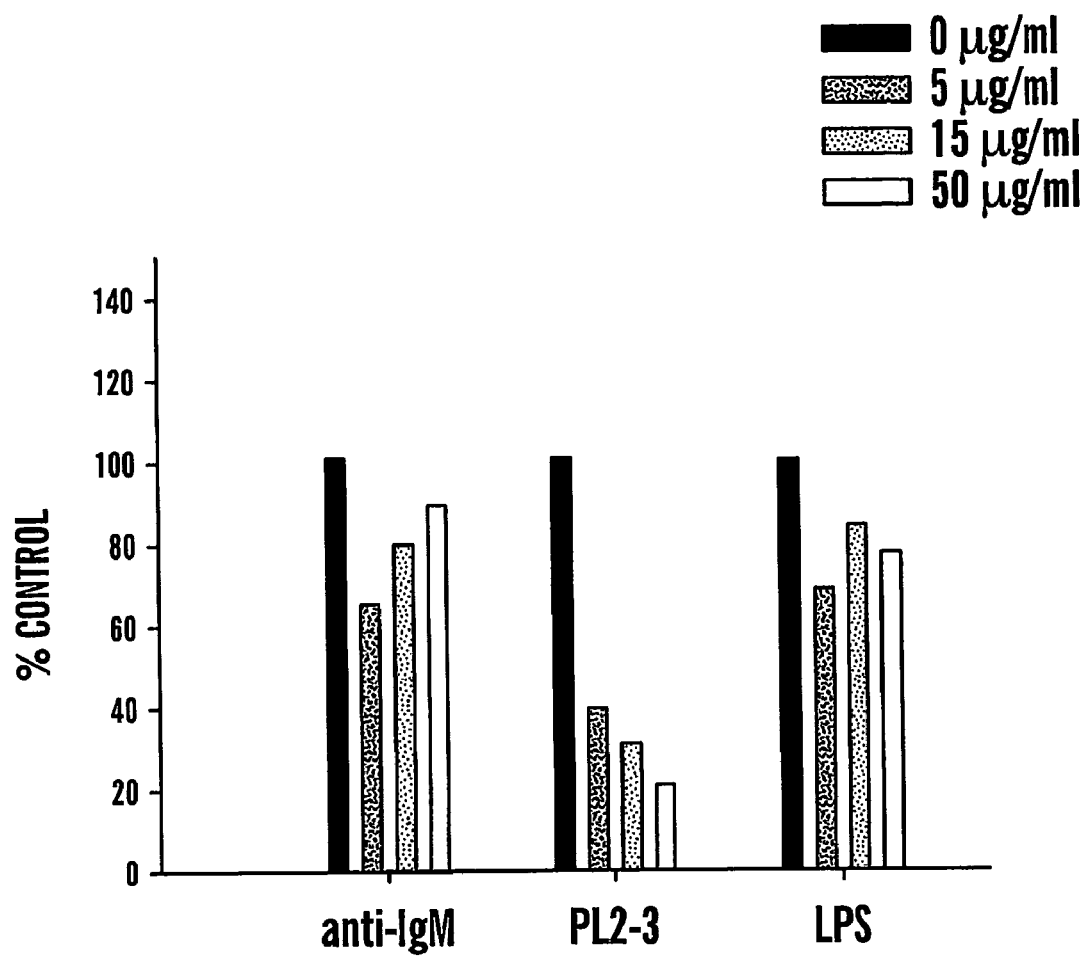
FIG. 1 shows that anti-nucleosome antibody (PL2-3) stimulation of AM14 RF+ B cells is DNase sensitive. The IgG2a anti-nucleosome antibody binds to chromatin released from the B cells in culture to form an immune complex which is recognized by the B cell via its IgG2a-specific antigen receptor. AM14 RF+ spleen cells were pre-incubated with various concentrations of DNase I (0, 5, 15, or 50 μg/ml) for 15 minutes prior to the addition of goat anti-mouse IgM F(ab')$_2$, PL2-3 (IgG2a' anti-nucleosome mAb), or LPS. Results are expressed as the percentage of the maximum response to each ligand in the absence of DNase.

The present invention provides methods and compositions for treating and/or preventing immune complex associated diseases (ICAD), in a subject having an ICAD or at risk for the ICAD.

For the purposes of this invention the term "immune complex associated diseases" or "ICAD" refers to diseases including, but not limited to systemic lupus erythematosus (SLE) and related connective tissue diseases, rheumatoid arthritis, hepatitis-C and hepatitis B related immune complex disease (e.g., cryoglobulinemia), Behcets disease, autoimmune glomerulonephritides, and vasculopathy associated with the presence of LDL/anti-LDL immune complexes.

We have discovered that immune complexes (IC) containing an autoantigen, such as chromatin, but not IC containing a foreign antigen, are able to activate autoreactive B cells and that this activation is dependent on the ability of the autoantigen-containing IC to sequentially engage both the B cell receptor and a second receptor, a Toll-like receptor. This finding establishes a novel link between the innate and adaptive immune systems and consequently a general mechanism whereby autoreactive B cells specific for protein/nucleic acid autoantigens are activated.

The Toll-like receptors (TLRs) are a family of membrane bound receptor proteins that are critically involved in innate immune responses and recognize pathogen associated molecular patterns or determinants that appear unique to microorganisms and are involved in activating immune cells against the source of these microbial particles.

The Toll-like family of receptors have leucine-rich repeats in their extracellular domains and the Toll/IL-1 receptor homology domain in their cytoplasmic domains. The Toll family is remarkably conserved in evolution. The first member discovered was the product of the toll gene which is part of the signaling pathway responsible for the specification of dorsal-ventral polarity in the early development of the fruit fly *Drosophila melanogaster.*

Currently ten mammalian homologues have been identified, called TLR1 through TLR10. Both the IL-1 receptor and the TLRs share similar downstream effects, such as the activation of immune response genes, and all these receptors work through signaling cascades that include the adaptor protein MyD88 (Mussio et al., Science 278:1612; Wesche et al., Immunity 7:837) which has been previously described as a myeloid differentiation protein (Lord et al., Oncogene 5:1095). In general, the different TLRs are thought to be activated by different types of microbial particles (Hemmi et al., Nature 408:740-745 (2000); Underhill et al., Nature 402: 39-43 (1999); Aliprantis et al., EMBO J., 19:3325-3336 (2000)). However, there is also accumulating evidence that in addition to microbial particles, mammalian TLRs can also recognize certain self (mammalian) antigens, in particular cytoplasmic components that are released from cells as a result of cell death (Akira et al., Nat Immunol., 2: 675-680 (2000).

The term "Toll-like receptor" is herein meant to include an intact Toll-like receptor, for example a receptor that has been described in the Online Mendelian Inheritance in Man under access numbers 601194 TOLL-LIKE RECEPTOR 1, TLR1; 603028 TOLL-LIKE RECEPTOR 2, TLR2; 603029 TOLL-LIKE RECEPTOR 3, TLR3; 603030 TOLL-LIKE RECEPTOR 4, TLR4; 603031 TOLL-LIKE RECEPTOR 5, TLR5; 605403 TOLL-LIKE RECEPTOR 6, TLR6; 300365 TOLL-LIKE RECEPTOR 7, TLR7; 300366 TOLL-LIKE RECEPTOR 8, TLR8; 605474 TOLL-LIKE RECEPTOR 9, TLR9; and 606270 TOLL-LIKE RECEPTOR 10. TLR10 or a functional fragment thereof such as, for example, a soluble form of the Toll-like receptor, i.e. where the membrane binding domain has been deleted or altered, in some embodiments the cytoplasmic domain is also not present, or a MyD88 binding or interacting fragment of the Toll-like receptor or a homolog of the Toll-like receptor capable of binding to or interacting with MyD88. More preferably the TLR is TLR9.

Our experiments to this point have identified the importance of the interaction between TLR9 and the chromatin component of the chromatin-containing immune complexes. However, in SLE and related diseases immune complexes commonly form with autoantibodies and distinct RNA/protein antigenic complexes including the Sm antigen and small nuclear ribonucleoproteins (snRNP) (Tan, E. *Adv. Immunol.* 44, 93-151 (1989)). In addition, in immune complex associated diseases such as hepatitis C, pathogenic immune complexes form between antibodies and the RNA containing viruses. TLR3 has been identified as a specific receptor for double-stranded RNA (Alexopoulou, Nature. 413, 732-738 (2001). Thus, it is reasonable to anticipate that TLR3 engagement will be important in the activation process elicited by these RNA-containing immune complexes.

Preferably the TLR is TLR3 or TLR 9, or a functional fragment thereof or a fragment that is homologous to TLR 3 or TLR 9 and capable of binding or interacting with MyD88.

The Toll-like receptor useful according to the present invention can also be a fusion receptor wherein the Toll-like receptor is fused with another protein such as a Myc-tag. The preferred Toll-like receptors include Toll-like receptor-2 or Toll/Interleukin-1 receptor-like 4 (Chaudhary, et al., *Blood* 91: 4020-4027, 1998), Toll-like receptor-3 (Rock, et al., *Proc. Nat. Acad. Sci.* 95: 588-593, 1998), and Toll-like receptor-9 (Chuang and Ulevitch, *Europ. Cytokine Netw.* 11: 372-378, 2000; Du, et al., *Europ. Cytokine Netw.* 11: 362-371, 2000) or functional fragments thereof or homologs that have a similar function, such as for example, binding MyD88.

As used herein, the terms "treatment" or "treating" include: (1) preventing such disease from occurring in a subject who may be predisposed to these diseases but who has not yet been diagnosed as having them; (2) inhibiting these diseases, i.e., arresting their development; or (3) ameliorating or relieving the symptoms of these diseases, i.e., causing regression of the disease states.

The compounds preferably inhibit activation of B cells (BC) or dendritic cells (DC) by at least about 50% in an in vitro or in vivo assays discussed below. More preferably the compounds inhibit autoantigenic activation of BCs or DCs via the Toll-like receptor by 75%, most preferably 95%. Additional compounds are identified and tested in the screening assays discussed in more detail below.

The compound useful according to the present invention is selected from a group consisting of compounds that bind components of the immune complex or Toll-like receptors. These compounds either prevent formation of the immune complex; prevent the autoantigen or the autoantigenic fragment of the immune complex from activating a Toll-like receptor (TLR) or prevent the downstream molecular signaling, such as that mediated through MyD88, from the Toll-like receptor. Such compounds include Toll-like receptor decoys, compounds that inhibit the activity of MyD88, compounds that inhibit production of immune complex components (e.g., antisense nucleotides)), dominant-negative TLR, a Toll-like receptor antagonist or blocker (such as ODN 2088 or antibodies against the TLRs), and compounds that inhibit signaling pathways activated by the interaction or binding of the autoantigenic fragment of the immune complex to the TLR. Preferably, the compound binds and/or inhibits function of Toll-like receptors TLR2, TLR3, and TLR9 or functional domains thereof. More preferably, the TLR is TLR3 or TLR9 or a functional fragment thereof.

The invention further provides efficient screening methods to identify pharmacological agents or lead compounds for agents which inhibit binding of the immune complex (or the autoantigenic component thereof) to the TLR, preferably TLR 2, TLR 3, TLR 9, or any combination thereof, most preferably TLR3 or TLR 9. The methods are amenable to automated, cost-effective high throughput drug screening and have immediate application in a broad range of pharmaceutical drug development programs.

Generally, these screening methods involve assaying for compounds that modulate, for example, the autoantigen interaction with a TLR, preferably TLR2, TLR3, TLR9, or any combination thereof, most preferably TLR3 or TLR 9. Still, more preferably the compound modulates interaction with TLR 9. A wide variety of assays for binding agents are provided including labeled in vitro protein-protein binding assays, immunoassays, cell based assays, etc.

In vitro binding assays employ a mixture of components including a TLR polypeptide, preferably TLR2, TLR3, TLR9, or any combination thereof, most preferably TLR3 or TLR9, still more preferably TLR9 which may be part of a fusion product with another peptide or polypeptide, e.g. a tag for detection or anchoring, etc. The assay mixtures may also comprise a natural intracellular TLR binding target, such as MyD88. While native full-length binding targets may be used, it is frequently preferred to use portions (e.g. peptides) thereof so long as the portion provides binding affinity and avidity to the subject MyD88 polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the TLR polypeptide specifically binds the cellular binding target, portion or analog with a reference binding affinity. The mixture components can be added in any order that provides for the requisite bindings and incubations may be performed at any temperature that facilitates optimal binding. Incubation periods are likewise selected for optimal binding but also minimized to facilitate rapid, high-throughput screening.

After incubation, the agent-biased binding between the TLR polypeptide and one or more binding targets is detected by any convenient way. A difference in the binding affinity of the TLR polypeptide to the target in the absence of the agent as compared with the binding affinity in the presence of the agent indicates that the agent modulates the binding of the TLR polypeptide to the TLR binding target. Analogously, in the cell-based assay also described below, a difference in TLR-dependent transcriptional activation in the presence and absence of an agent indicates the agent modulates TLR function, for example, binding to MyD88. A difference, as used herein, is statistically significant and preferably represents at least a 50%, more preferably at least a 75%, still more preferably at least a 90% difference.

The preferred assay to test a pharmaceutical agent for potency of interrupting the activation of B cells or dendritic cells comprises RF+ B cells or dendritic cells which are incubated with a test agent and a TLR stimulatory agent, such as PR1-3, PL2-3, or a CpG S-ODN 1826 (see, e.g. Leadbetter et al., Nature, 416:603-607, 2002) in a suitable cell culture medium. Incubation with the test agent can be performed prior to or simultaneously with the addition of the stimulatory agent.

The activation of the B cells can be observed using a number of techniques well known to one skilled in the art. Fore example, the $^3$[H] thymidine incorporation assay can be performed to measure proliferation of B cells. Alternatively, activation of B cells can be analyzed using fluorescence activated cell sorting (FACS) to measure cell surface expression of, for example, CD80, CD86 or MHC class II molecules. Activation of dendritic cells can be observed by measuring production of cytokines, such as TNF-α, interferon-α, IL-12 and BAFF, or co-stimulatory molecules such as CD80, CD86 or MHC class II molecules (Banchereau, et al., *Annu. Rev. Immunol.* 18: 767-811, 2000; Mackay and Browning, *Nat. Rev. Immunol.* 2:465-475).

Alternatively, dendritic cell activation can be observed by measuring morphologic changes in the DC (Banchereau, et al., *Annu. Rev. Immunol.* 18: 767-811, 2000).

If the stimulation of the expression of, for example a co-stimulatory molecule is decreased as a result of adding the test agent, the test agent is considered to be a potential agent to treat ICAD. The expression is considered decreased if it is at least about 50%, more preferably at least about 60-75%, most preferably at least about 90% decreased as compared to a cell sample where no test agent has been added. More detailed examples are given in the Examples in the end of this section.

A preferred assay mixture of the invention is set forth in the Examples. An assay mixture of the invention also comprises a candidate pharmacological agent. Generally, a plurality of assay mixtures are run in parallel with different candidate agent concentrations to obtain a differential response to the various concentrations. Typically, one of these assay mixtures serves as a negative control, i.e. at zero concentration or below the limits of assay detection. Candidate agents encompass numerous chemical classes, though typically they are organic compounds and preferably small organic compounds. Small organic compounds suitably may have e.g. a molecular weight of more than about 50 yet less than about 2,500. Candidate agents may comprise functional chemical groups that interact with proteins and/or DNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides and peptides. Alternatively, libraries of natural compounds in the form of bacterial, fungal, plant and animal extracts are available or readily produced. Libraries can be composed of small polypeptides (see, for instance, Lam et al., Nature, 354: 82, 1991 and WO 92/00091; Geysen et al., J Immunol Meth, 102: 259, 1987: Houghten et al., Nature, 354: 84, 1991 and WO 92/09300 and Lebl et al., Int J Pept Prot Res, 41, 201, 1993). Alternatively, libraries of small non-peptide molecules can be based upon a common template or core structure (see, for instance, Ellman and Bunin, J Amer Chem Soc, 114:10997, 1992 for benzodiazepine template; WO 95/32184 for oxazolone and aminidine template; WO 95/30642 for dihydrobenzopyran template and WO 95/35278 for pyrrolidine template.

Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc.

Antibodies and binding fragments thereof or aptamers (available from, for example SomaLogic Inc., Boulder, Colo.) that bind immune complex components and prevent formation or TLR binding are also useful. Examples of antibodies useful according to the invention include monoclonal antibodies against TLRs such as anti-TLR3 monoclonal antibody (Matsumoto et al., Biochem. Biophys. Res. Commun., 293:1364-1369, 2002) anti-TLR-9. (Toll-like receptor 9, Imgenex, San Diego, Calif.) or humanized versions thereof.

The term dominant negative Toll-like receptor as used herein refers to Toll-like receptors, that have been engineered to have a defect, such as deletion of the domain required for downstream signaling but which can bind the antigenic portion of the immune complex.

The antibodies and binding fragments thereof can be either polyclonal or monoclonal, but preferably are monoclonal. If polygonal, the antibodies can be in the form of antiserum or monospecific antibodies, such as purified antiserum which has been produced by immunizing animals with purified protein. Preferably, however, the antibodies are monoclonal antibodies so as to minimize the administration of extraneous proteins to an individual. Monoclonal antibodies can be prepared according to well known protocols. See. e.g., Skare et al., *J. Biol. Chem.* 268: 16302-16308 (1993); and U.S. Pat. Nos. 4,918,163 and 5,057,598, which are incorporated herein by reference. The antibodies can be whole, Fab's, single chain, single domain heavy chain, etc. Single chain antibodies are preferable. Methods for the production of single chain binding polypeptides are described in detail in, e.g., U.S. Pat No. 4,946,778, which is incorporated herein by reference.

When an antibody or other protein or peptide is used the peptide is preferably conjugated to a carrier such as biotin or a poly(alkaline oxide), for example polyethylene glycol (PEG). Polymeric substances such as dextran, polyvinyl pyrrolidones, polysaccharides, starches, polyvinyl alcohols, polyacryl amides or other similar polymers can be used. The poly(alkaline oxide) can include monomethoxy polyethylene glycol, polypropylene glycol, block copolymers of polyethylene glycol and the like. Polyethylene glycol as poly(alkylene oxide) is preferred. The polymers can also be distally capped with $C_{1-4}$ alkyls instead of monomethoxy groups.

For administration to humans, e.g., as a component of a composition for in vivo treatment, the monoclonal antibodies are preferably substantially human or humanized to minimize immunogenicity, and are in substantially pure form. By "substantially human" is meant that the immunoglobulin portion of the composition generally contains at least about 70% human antibody sequence, preferably at least about 80% human, and most preferably at least about 90-95% or more of a human antibody sequence.

For therapeutic applications, the compounds may be suitably administered to a subject such as a mammal, particularly a human, alone or as part of a pharmaceutical composition, comprising the compounds together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal, parenteral (including subcutaneous, intramuscular, intravenous and intradermal), ocular using eye drops, transpulmonary using aerosolubilized or nebulized drug administration. The formulations may conveniently be presented in unit dosage form, e.g., tablets and sustained release capsules, and in liposomes, and may be prepared by any methods well know in the art of pharmacy. (See, for example, Remington: The Science and Practice of Pharmacy by Alfonso R. Gennaro (Ed.) 20th edition, Dec. 15, 2000, Lippincott, Williams & Wilkins; ISBN: 0683306472.)

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

It will be appreciated that actual preferred amounts of a given compound used in a given therapy will vary according to the particular compound being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

The present invention also provides methods for diagnosing ICAD in an individual. The method comprises of measuring the Toll-like receptor mediated activation of a B cell or dendritic cell induced by a biological sample containing an immune complex(es) consisting of autoantigen(s) and autoantibody(ies). Activation of a Toll-like receptor in B cells can be measured indirectly, for example by measuring proliferation of the B cells, expression of various co-stimulatory molecules such as CD80, CD86 or upregulation of MHC class II molecules. Activation of Toll-like receptor in dendritic cells can be measured by observing morphologic changes of the dendritic cells either with or without specific staining, or by measuring expression of co-stimulatory molecules such as CD80 and CD86, or by measuring upregulation of activation markers such as CD69, or by measuring upregulation of chemokine receptors such as CCR7, or by measuring the production of cytokines such as TNF-α using a number of different techniques including assaying mRNA or protein levels.

For example, change in the expression of INFα can be measured using RNA isolated from dendritic cells. RNA quantitation methods include polymerase chain reaction (PCR) based methods such as, for example, a TaqMan® system (Applied Biosystems), Brilliant Quantitative PCR (Stratagene), Platinum® quantitative PCR (Resgen, Inc.). RNA is isolated from a biological sample, for example blood sample, which is taken from an individual suspected of having ICAD. The amount of Toll-like receptor mRNA is quantified using, for example, techniques listed above and compared to a sample from a control individual.

Preferably, assays such as FACS analysis are used to measure protein expression of the co-stimulatory molecules. If the expression of these co-stimulatory molecules is increased, it indicates that the individual is affected with an ICAD. The activity is considered increased if the assay shows at least about 5% increase in the amount of the co-stimulatory molecule compared to the control sample.

Alternatively, serum from a test individual suspected of having ICAD can be injected to a cell culture expressing a functional Toll-like receptor pathway. The activity of the Toll-like receptor is consequently measured from the cell culture treated, in parallel, with control and test subject serum. If the activity of the Toll-like receptor is increased in the cells treated with the test individual's serum compared to the cells treated with the control serum, it indicates that the individual is affected with an ICAD. The expression is considered increased if it is at least about 5% higher than in the control sample.

It is to be understood that while the invention has been described in conjunction with the preferred specific embodiments thereof that the foregoing description as well as the examples that follow are intended to illustrate and not limit the scope of the invention. Other aspects, advantages and modification within the scope of the invention will be apparent to those skilled in the art to which the invention pertains.

EXAMPLE 1

Autoreactive B cells are present in the lymphoid tissues of healthy individuals, but typically remain quiescent. When this homeostasis is perturbed, the formation of self-reactive antibodies can have serious pathological consequences. B cells expressing an antigen-receptor specific for self-IgG make a class of autoantibodies known as rheumatoid factor (RF). Here we show that effective activation of RF+ B cells is mediated by IgG2a/chromatin immune complexes and requires the sequential engagement of the antigen-receptor and a MyD88-dependent Toll-like receptor family member. These data establish a critical link between the innate and adaptive immune systems in the development of systemic autoimmune disease and explain the preponderance of autoantibodies reactive with nucleic acid/protein particles. The unique features of this dual-engagement pathway should facilitate the development of therapies that specifically target autoreactive B cells.

We have now developed a model in vitro system for analyzing the factors involved in the activation of autoreactive B cells and dendritic cells in autoimmune disease. One of the prevalent autoantibody specificities in lupus-prone lpr mice is rheumatoid factor (RF). RFs are antibodies that are reactive with self IgG. RF B cells become activated, expand in number, and differentiate into antibody secreting cells in autoimmune strains of mice, but not in mice of a non-autoimmune background. In order to investigate the mechanisms involved in this pathologic activation, we studied primary RF+ B cells from the spleens of mice genetically engineered to express a pair of transgenes which would confer a particular RF specific to most B cells. These B cells are prototypes of the autoreactive B cells found in SLE patients.

Initially, we demonstrated that these RF+ B cells were activated by serum samples from autoimmune mice, but not by serum form non-autoimmune mice (Rifkin et al, 2000). We further proved that the stimulatory factor in the serum was, in fact, IgG2a. However, comparable amounts of IgG2a isolated from non-autoimmune sera were not stimulatory, indicating that not all IgG2a was sufficient to stimulate RF+ B cells. Therefore we concluded that IgG2a in the autoimmune sera had unique properties. To further identify the relevant IgG2a component, we used IgG2a monoclonal antibodies (mAbs) and showed that mAbs specific for self-antigens, such as DNA-histone complexes, were stimulatory while antibodies specific for foreign or non-self antigens were not stimulatory.

Figure 2A:
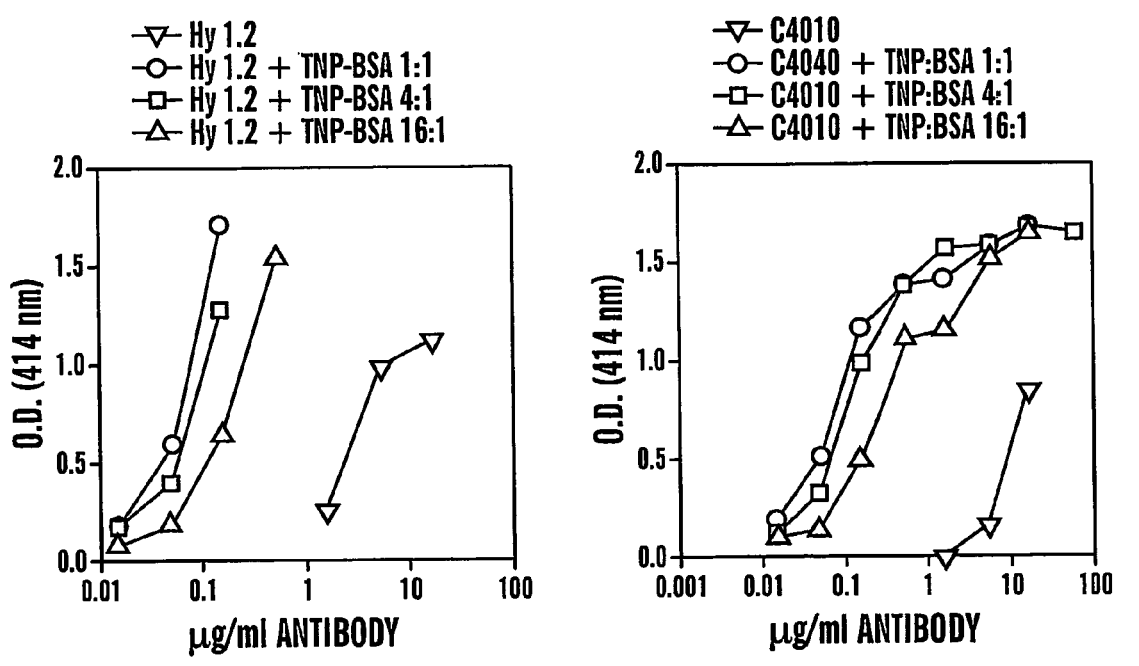
FIGS. 2A-2B show that anti-TNP/TNP-BSA IC fail to efficiently stimulate AM14 RF+ B cell proliferation. The anti-TNP mAbs Hy1.2 (IgG2a$^a$) and C4010 (IgG2a$^b$) were mixed with varying concentrations of TNP-BSA [50 µg/ml (circle), 12.5 µg/ml (square), 3.1 µg/ml (up-triangle)] to form IC with antibody/protein ratios of 1:1, 4:1, and 16:1 respectively.
Figure 2B:
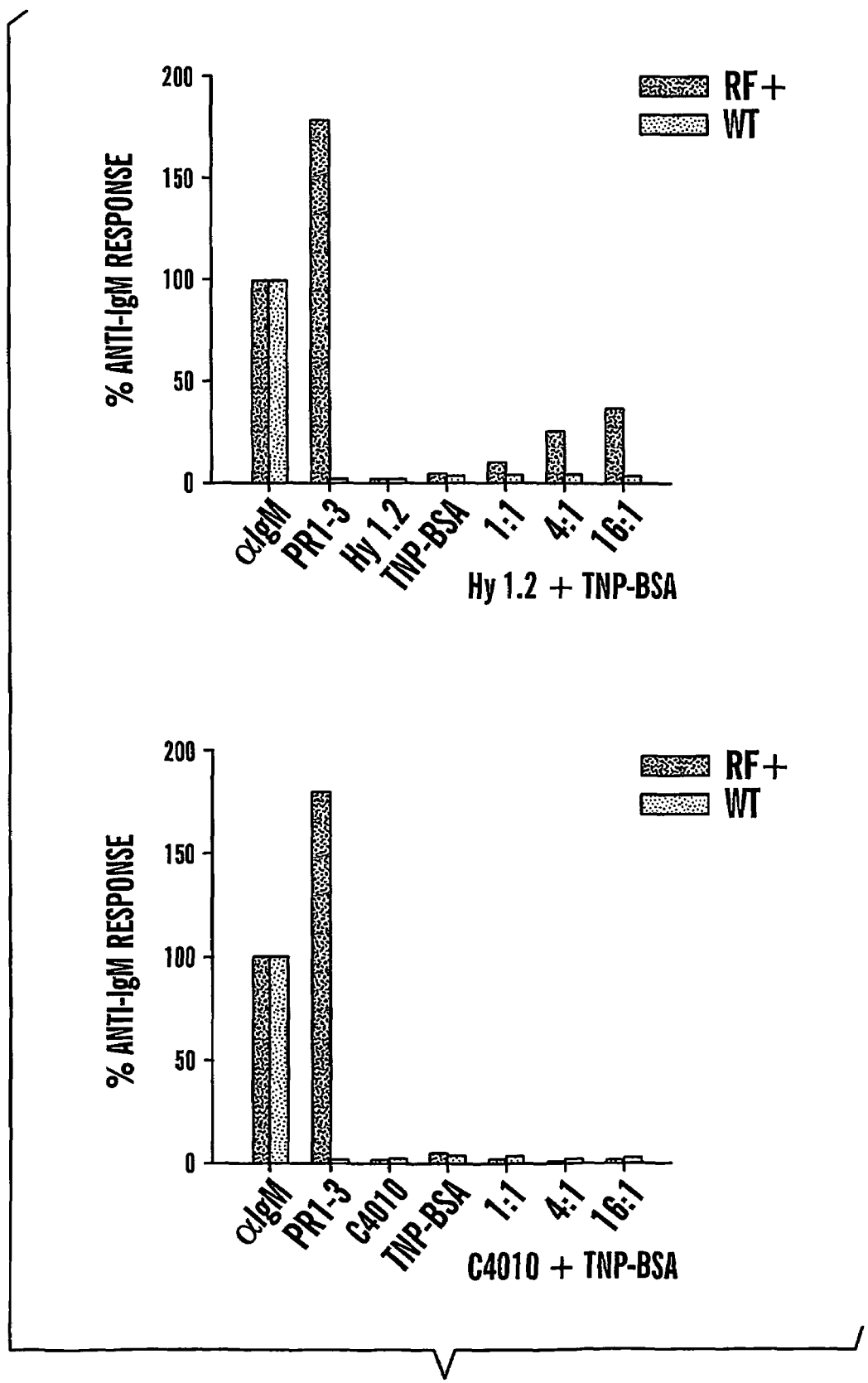

We next considered the possibility that autoantibody/autoantigen immune complexes were the relevant component. When the assays with sera and mAbs were run in the presence of DNAse, stimulation of the RF+ B cells was dramatically reduced (FIG. 1). These data suggested that cleavage of the DNA backbone results in the dissociation of the autoantibody/autoantigen (DNA) immune complex. This strongly indicates that immune complexes of autoantigens/autoantibodies have unique properties which preferentially activate autoreactive B cells. The inability of immune complexes containing non-self antigen to activate autoreactive B cells is shown in FIG. 2.

Figure 4A:
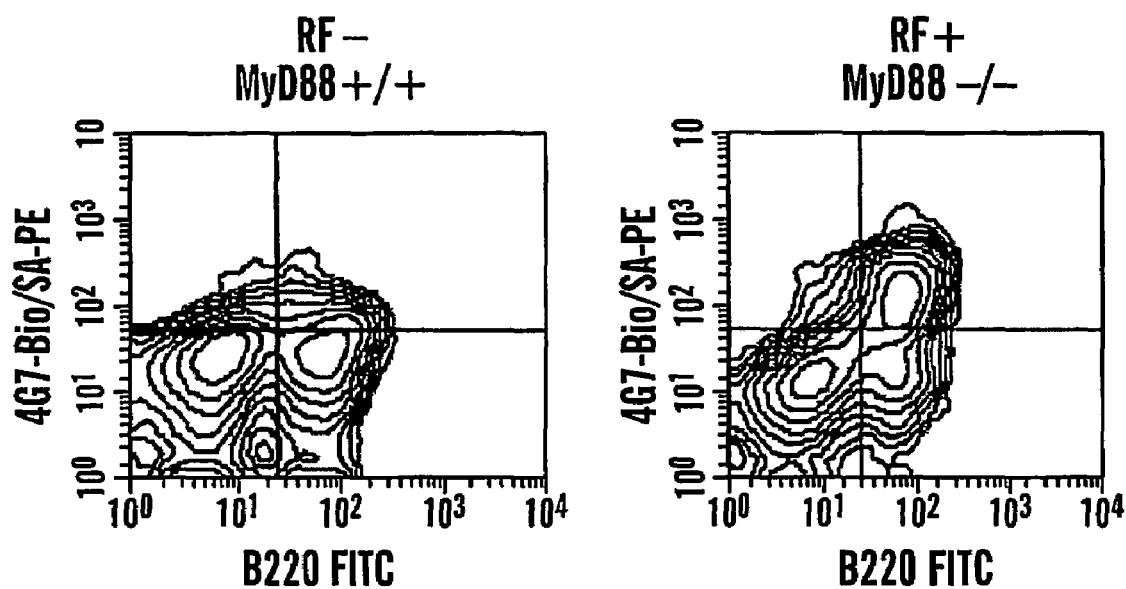
FIGS. 4A-4C show that autoAb/autoAg-IC stimulation of RF+ B cells is MyD88-dependent.
Figure 4B:
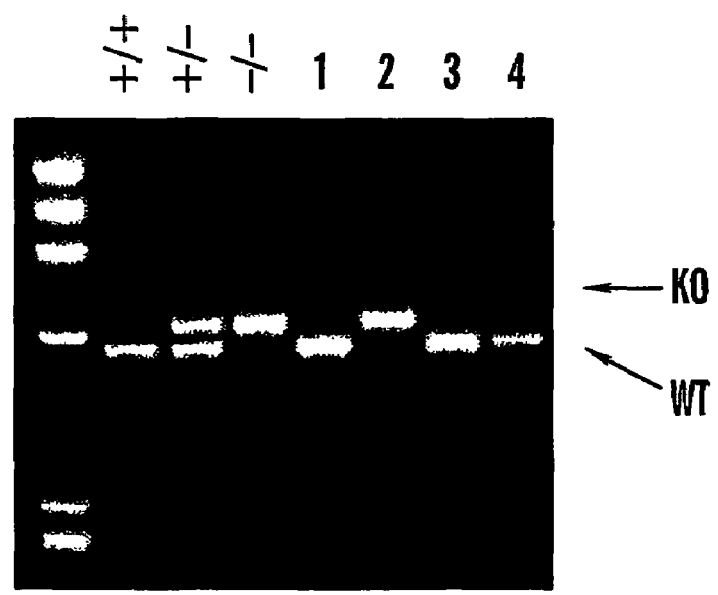

We investigated the possibility that autoantibody/autoantigen immune complexes are capable of engaging a second receptor, which then facilitates the activation of the RF B cells. Since recent studies have shown that a family of proteins known as Toll-like receptors (TLR) can bind to bacterial DNA and lead to macrophage, dendritic cell and B cell activation, we considered the possibility that TLR could play a role in the activation of these autoreactive RF B cells. TLR are currently a very popular area of study, and have been shown to be responsible to binding and recognition of many pathogen-associated molecular patterns (PAMPS), so this link to innate immune responses would be a very unique connection for autoimmunity. All known mammalian TLR signal through the adaptor protein, MyD88. TLR-mediated activation in mice in which the MyD88 gene has been eliminated by genetic engineering is severely compromised and signals mediated through TLR9 are completely abolished. We bred our transgenic RF+ mice onto a MyD88−/− background. The resulting mice were positive for the RF transgenes (FIG. 4A) and lacked MyD88 signaling molecules (FIG. 4B).

Figure 4C:
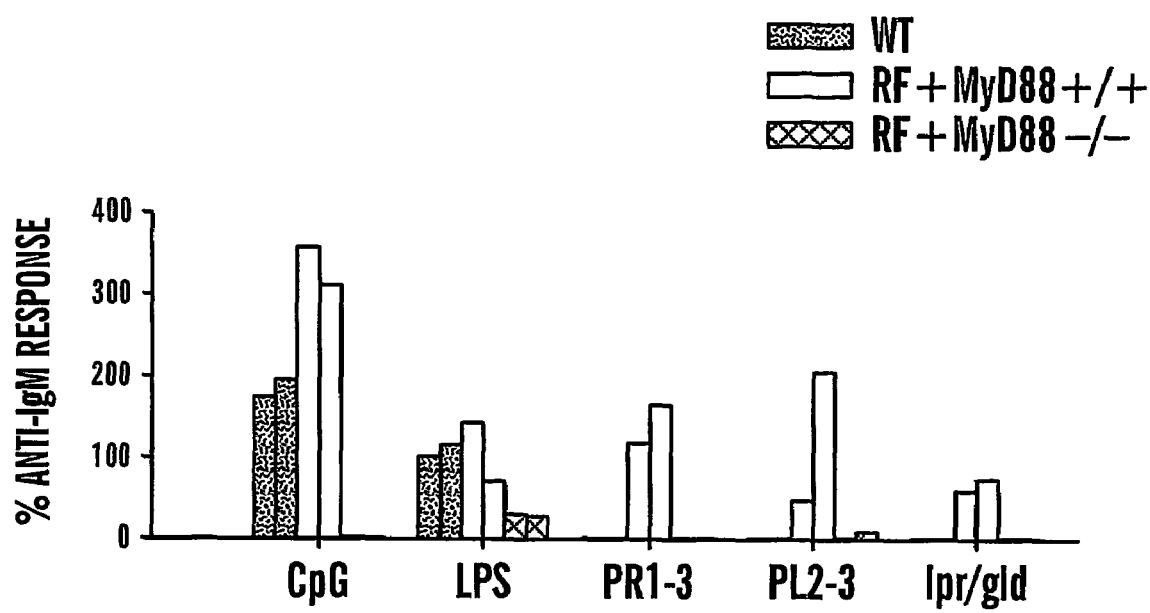

We found that RF MyD88−/− mice fail to respond to any of the autoantibodies which otherwise stimulate proliferation of RF MyD88+/+ B cells (see FIG. 4C). We tested multiple forms of autoantibodies: serum, antinucleosome antibodies and anti-Sm antibodies. This is consistent with the hypothesis that autoantibody/autoantigen immune complexes contain repeating pattern components such as DNA or RNA which engage Toll receptors either inside the B cell (DNA/TLR9) or on the surface of the B cell (RNA/TLR3). In the case of autoreactive RF+ B cells, the autoantigen/autoantibody immune complexes likely sequentially engage the BCR and the TLR, leading to increased activation and proliferation. This is the first demonstration that co-engagement of the BCR and TLR can result in the activation of autoreactive B cells. This connection provides a very unique link between autoimmunity and the body's innate immune response and may provide an initiating mechanism for many of the pathogenic responses in autoimmune diseases such as SLE and rheumatoid arthritis.

Subsequent studies demonstrated that drugs known to block B cell activation by stimulatory CpG ODN via TLR9, such as chloroquine and concanamycin A, completely blocked the ability of the chromatin containing IC to stimulate RF+ B cells. The response could also be blocked by inhibitory CpG ODN which specifically inhibits activation through TLR9. These data demonstrate that TLR9 is a key receptor in the activation of autoreactive B cells. The data demonstrate that the IgG component of the immune complex binds to the BCR leading to the internalization of the immune complex and delivery to an internal vesicular compartment. The subsequent engagement of TLR9 by the chromatin component of the IC within this internal compartment leads to B cell activation. Factors that contribute to the enhanced availability and thus uptake of chromatin per se (susceptibility factors for SLE) could also lead to B cell activation through a similar mechanism. It is of note that anti-chromatin antibodies are the first detectable autoantibody present in the sera of SLE patients and animals models of spontaneous SLE.

EXAMPLE 2

Patients afflicted with SLE and other systemic autoimmune diseases produce a wide range of autoantibody specificities. Very frequently these autoantibodies bind to chromatin or other subcellular nucleic acid/protein particles (Tan, E. *Adv. Immunol.* 44, 93-151 (1989)). MRL/lpr mice, a well-studied murine model of systemic lupus erythematosus and rheumatoid arthritis, also produce exceedingly high titers of IgG anti-IgG rheumatoid factor (RF) (Theofilopoulos, et al., *J. Exp. Med.* 162, 1-18 (1985); Wolfowicz, et al., *Clin. Immunol. Immunopath.* 46, 382-395 (1988)). This RF response has provided a highly relevant transgenic model for the study of autoantibody regulation. B cells from the AM14 transgenic mouse line express an antigen receptor specific for IgG2a$^{a/j}$, originally captured as a hybridoma product from the spleen of a diseased MRL/lpr mouse (Shlomchik, et al., *Int. Immunol.* 5, 1329-1341 (1993)). The AM14 allotype specificity and relatively low affinity for monomeric IgG2a are typical of the disease associated RF repertoire (Jacobson, et al., *J. Immunol.* 152, 4489-99 (1994)). In wildtype mice, AM14 RF+ B cells develop normally and remain functionally naïve (Hannum, et al., *J. Exp. Med.* 184, 1269-1278 (1996)). However, on an autoimmune-prone lpr background of the cognate allotype, they become activated, proliferate and secrete autoantibody (Wang, and Shlomchik, *J. Exp. Med.* 190, 639-649 (1999)). A number of factors are likely to contribute to the activation of AM14 B cells in lpr mice, not the least of which is the status of the autoantigen, IgG2a.

RF+ B Cells Are Activated by Autoantibody/Autoantigen Immune Complexes

We have previously shown that AM14 RF+ B cells can be activated in vitro by IgG2a$^{a/j}$ isolated from the sera of autoimmune mice, but not by comparable levels of IgG2a present in sera obtained from wildtype mice (Rifkin, et al., *J. Immunol.* 165, 1626-1633 (2000)). RF+ B cells were also found to proliferate strongly in response to affinity purified IgG2a$^{a}$ mAbs specific for nucleosomes, a self-antigen, whereas IgG2a$^{a/j}$ mAbs specific for haptens or other foreign antigens produced little, if any, response (Rifkin, et al., *J. Immunol.* 165, 1626-1633 (2000)). These studies suggested that immune complexes (IC) formed between IgG2a nucleosome-specific mAbs and chromatin fragments released from co-cultured cells (Emlen, et al., *J. Immunol.* 148, 3042-3048 (1992)) could effectively activate RF+ B cells, while monomeric anti-hapten IgG2a antibodies could not. To further test this premise, DNase was added to the assay medium as a means of disrupting the putative IC. The vigorous proliferative response normally elicited by the purified anti-nucleosome mAb PL2-3 (Monestier and Novick *Mol. Immunol.* 33, 89-99 (1996)) or by autoimmune serum was dramatically reduced (FIG. 1). Nonspecific toxicity of the DNase was not a factor as the responses to F(ab')$_2$ anti-IgM and LPS were unaffected (FIG. 1). These data confirm that RF+ B cells respond to IgG2a IC that contain DNA, not to monomeric IgG2a antibodies alone.

If RF+ B cell activation by IgG2a IC simply resulted from more effective crosslinking of the antigen receptor than would be possible with monomeric IgG2a, then conventional anti-hapten/hapten-protein complexes should also strongly stimulate RF- B cells. To address this issue, ICs were prepared by pre-incubating IgG2a monoclonal anti-TNP antibodies with varying concentrations of TNP-BSA; complex formation was confirmed by demonstrating an increase in C1q binding activity (FIG. 2a). As expected, IC of C4010, an IgG2a$^b$ anti-TNP mAb, failed to stimulate RF+ B cells at all anti-TNP/TNP-BSA ratios. Surprisingly, IC of Hy1.2, an IgG2a$^a$ anti-TNP mAb, only elicited a very modest proliferative response relative to that elicited by anti-nucleosome mAb-containing IC. This discrepancy indicated that the extent of RF+ B cell proliferation elicited by an IC depends on both the antibody and the nature of the (auto)antigen.

Activation by IC is Not Dependent on Complement Receptor Co-Engagement

Figure 3:
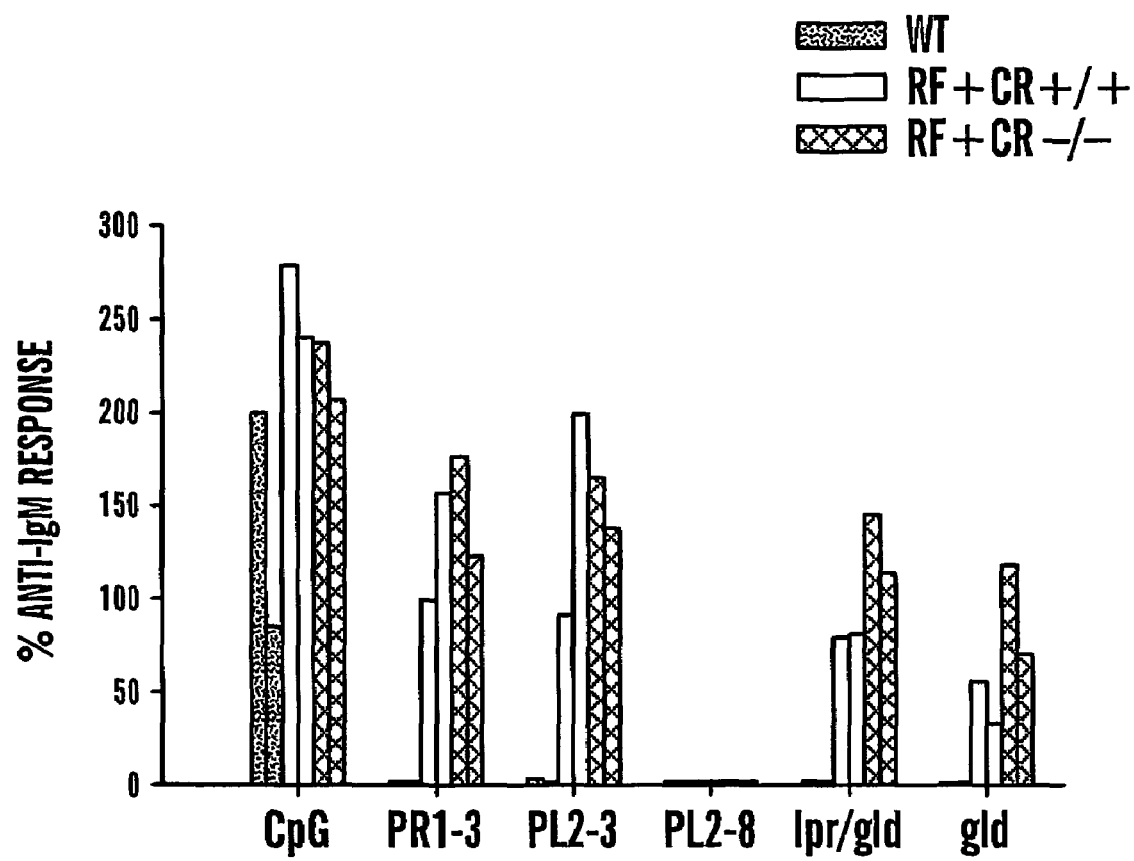
FIG. 3 shows that autoantibody/autoantigen-IC stimulation of RF+ B cells is not complement receptor dependent. Spleen cells from each of two WT control mice (gray), RF+ CR+/+ mice (white), and RF+ CR−/−mice (hatched) were stimulated with goat anti-mouse IgM F(ab')$_2$, CpG S-ODN 1826, the anti-nucleosome mAbs PR1-3 (IgG2a$^j$), PL2-3 (IgG2a$^j$), PL2-8 (IgG2b), or 3% serum from representative autoimmune mice (lpr/gld and gld).

A possible explanation for the dramatic difference in stimulatory capacity of the anti-nucleosome and anti-TNP IC was that only the former could synergistically engage both the B cell receptor (BCR) and a second receptor on the B cell surface. One potential candidate receptor was the complement receptor CD21, as complement components have been shown to bind autoantigen IC and could, in theory, serve to effectively co-engage CD19/CD21 and the BCR (Carter et al., *J. Immunol.* 141, 457-463 (1988)). However, when the AM14 heavy and light chain transgenics were bred onto mice deficient for CR1/2Cr2 (Ahearn, et al. *Immunity* 4, 251-262 (1996)), RF+ B cells from the CR1/2-deficient and CR1/2-sufficient littermates responded comparably to IgG2a anti-nucleosome mAbs and autoimmune sera (FIG. 3). B cells from control RF– littermates failed to respond to any form of IgG2a, confirming the specific nature of the ligands used in this study. A mitogenic hypomethylated CpG oligodeoxynucleotide was included as a control stimulus. These data demonstrate that complement receptors are not required for the RF+ B cell response to autoantibody/autoantigen IC.

Role of a MyD88-Dependent Receptor

Potential candidate receptors included members of the Toll-like receptor (TLR) family. These pattern recognition receptors were first described in *Drosophila* where they were shown to trigger the release of anti-fungal peptides (Lemaitre et al., *Cell* 86, 973-983 (1996)). Subsequently identified mammalian homologues were found to recognize a series of conserved microbial products (i.e. LPS, microbial lipoproteins, and hypomethylated CpG DNA) referred to as pathogen associated molecular patterns (AMPS) (Medzhitov, et al., *Nature* 388, 323-324 (1997); Akira, et al., *Nat. Immunol.* 2, 675-680 (2001)). Initial studies focused on the effects of microbial products on cells of the innate immune system where they were found to stimulate the release of a wide range of inflammatory mediators (Akira, et al., *Nat. Immunol.* 2, 675-680 (2001)). However, it was later shown that in addition to exogenous microbial ligands, TLRs could also recognize endogenous ligands released from damaged or stressed mammalian cells (Li, et al., *J. Immunol.* 166, 7128-7135 (2001)). All known mammalian TLRs signaling pathways use the adapter protein MyD88 (Akira, et al., *Nat. Immunol.* 2, 675-680 (2001)), although in the case of TLR4, an additional MyD88-independent pathway has been described (Horng, et al., *Nat. Immunol.* 2, 835-841 (2001)).

To investigate the potential role of TLRs in mediating RF+ B cell responses to autoantibody/autoantigen IC, we crossed the AM14 transgenes onto a MyD88–/– background (Adachi, et al., *Immunity* 9, 143-150 (1998)). B cells from RF– MyD88+/+ (wildtype), RF+ MyD88+/+, and RF+ MyD88–/– offspring, identified by a combination of PCR and FACS analysis (FIGS. 4A-4B), were assessed for their ability to respond to anti-IgM, CpG ODN, and LPS, as well as to a panel of anti-nucleosome mAbs and autoimmune sera. B cells from the MyD88-deficient mice responded normally to anti-IgM, but were unable to respond to stimulatory CpG DNA (Hacker, et al., *J. Exp. Med* 192, 595-600 (2000)). Their response to LPS was much lower than in wildtype mice, but still detectable, consistent with partial activation through MyD88, and responded only weakly to LPS, which is known to stimulate partially through a MyD88-independent mechanism (Horng, et al., *Nat. Immunol.* 2, 835-841 (2001)) (FIG. 4C). Most dramatically, B cells from the RF+ MyD88-deficient mice were completely unresponsive to the anti-nucleosome mAbs PR1-3 or PL2-3 or to any of the autoimmune sera that effectively stimulated RF+ MyD88+/+ B cells (FIG. 4C). These results clearly demonstrate that autoantibody/autoantigen IC are particularly stimulatory for RF+ B cells because they synergistically engage both the BCR and a MyD88-dependent receptor.

Figure 5A:
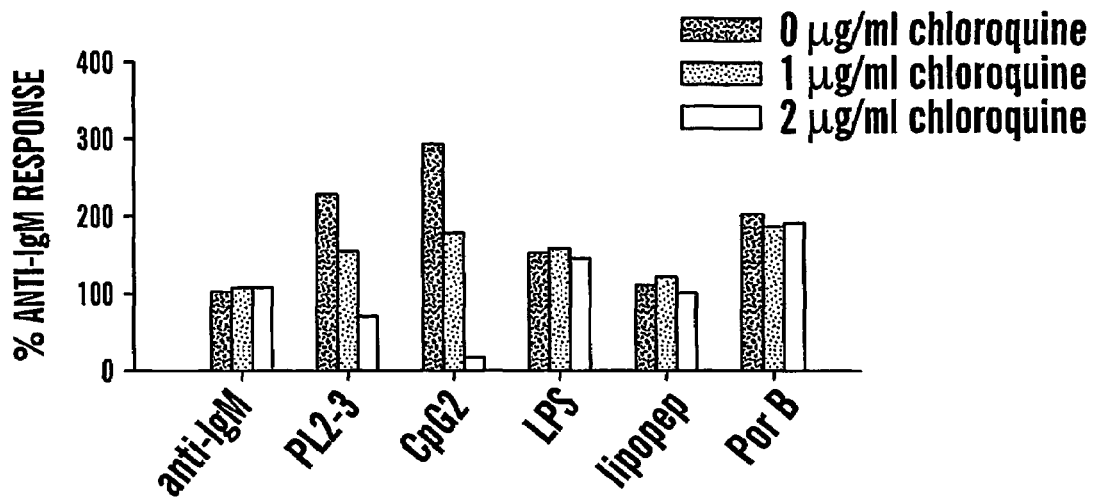
FIGS. 5A-5C demonstrate that autoAb/autoAg-IC stimulation of RF+ B cells can be blocked by inhibitors of the TLR9 signaling pathway.
Figure 5B:
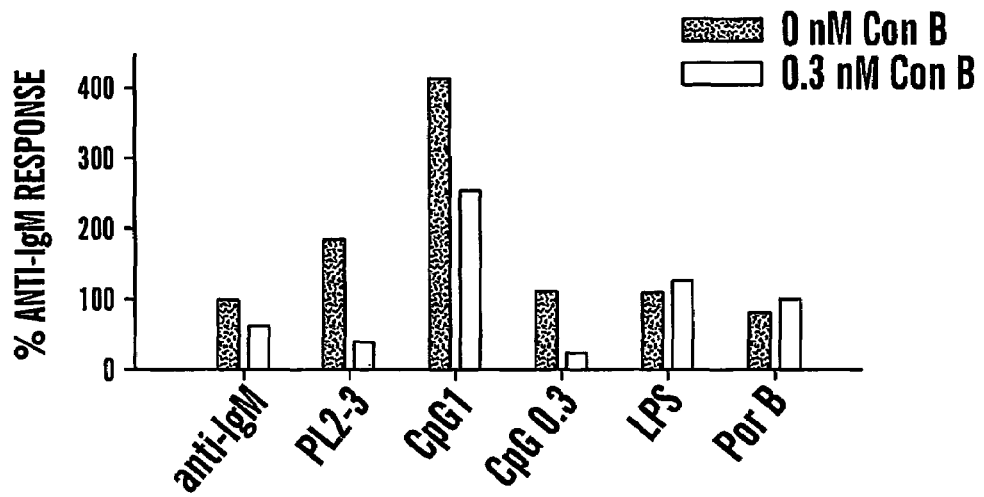

Hypomethylated CpG motifs are a common feature of bacterial DNA, but they are also present in mammalian DNA promoter elements (Singal and Ginder *Blood* 93, 4059-4070 (1999)). Since the B cell response to CpG oligodeoxyribonucleotides (ODN) is mediated through TLR9 (Hemmi, et al., *Nature* 408, 740-745 (2000)), we hypothesized that chromatin-containing IC could stimulate RF B cells by co-engaging TLR9. The TLR9-mediated response to CpG S-ODN is distinguished from other known TLR signaling pathways by its presumed requirement for endosome acidification and/or maturation as determined by sensitivity to chloroquine and ammonium chloride (Yi, et al., *J. Immunol.* 160, 4755-4761 (1998); Hacker, et al., *EMBO J.* 17, 6230-6240(1998)). Concanamycin B and bafilomycin A are specific inhibitors of the V-type ATPase responsible for acidification of endosomes (Benaroch, et al., *EMBO J.* 14, 37-49 (1995)). To evaluate the role of TLR9 in the activation of RF+ B cells, the effect of chloroquine, concanamycin B, bafilomycin A, and ammonium chloride on the stimulatory capacity of mAb PL2-3 and known TLR2 (lipopeptide, porin B) (Massari, et al., *J. Immunol.* 168:1533-1537, 2002), TLR4 (LPS), and TLR9 (CpG S-ODN 1826) ligands was determined. As expected, chloroquine inhibited the CpG S-ODN response and these inhibitors had little effect on the response to the TLR2 and TLR4 ligands. Notably, all four agents that blocked chloroquine also inhibited the RF+ B cell response to mAb PL2-3 (FIGS. 5A and 5B). The link to chloroquine is intriguing, as chloroquine is an effective treatment for autoimmune diseases including rheumatoid arthritis and SLE (Canadian Hydroxychloroquine Study Group, *N. Engl. J. Med.* 324, 150-154 (1991); Furst, et al., *Arth. Rheu.* 42, 357-365 (1999)). Our data therefore suggest that the therapeutic effects of chloroquine are due, at least in part, to its ability to interfere with TLR-mediated signals that contribute to autoantibody production or the production of proinflammatory mediators.

Figure 5C:
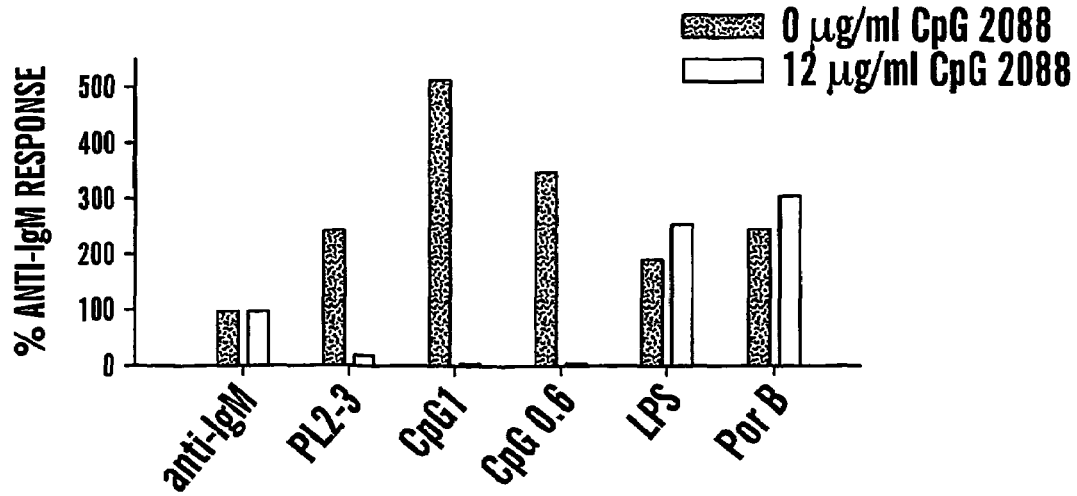
Figure 6A:
FIGS. 6A-B show the results of an experiment where MyD88-deficient (MyD88−/−) Fas-sufficient mice were bred with MyD88-sufficient (MyD88+/+) Fas-deficient (lprlpr) autoimmune mice to generate MyD88−/− lpr/lpr mice, and appropriate control groups. Anti-nuclear-antibodies (ANA) in the sera of age-matched MyD88+/+ lprlpr (FIG. 6A) and MyD88−/− lpr/lpr (FIG. 6B) littermates (12-13 weeks of age) were detected by indirect immunofluorescence using HEp-2 cells as substrate as previously described (Rifkin et al., Journal of Immunology. 161: 5164-5170, 1998). Serum from a diseased autoimmune MRL-lpr/lpr mouse served as the positive control and serum from a non-autoimmune BALB/c mouse as the negative control. This in vivo experiment demonstrates that, in a standard and widely used lupus mouse strain, autoantibody production requires signaling through MyD88. This strongly suggests that TLR activation is required for the development of lupus in this model.
Figure 6A:
Figure 6B:
Figure 6B:
Figure 7A:
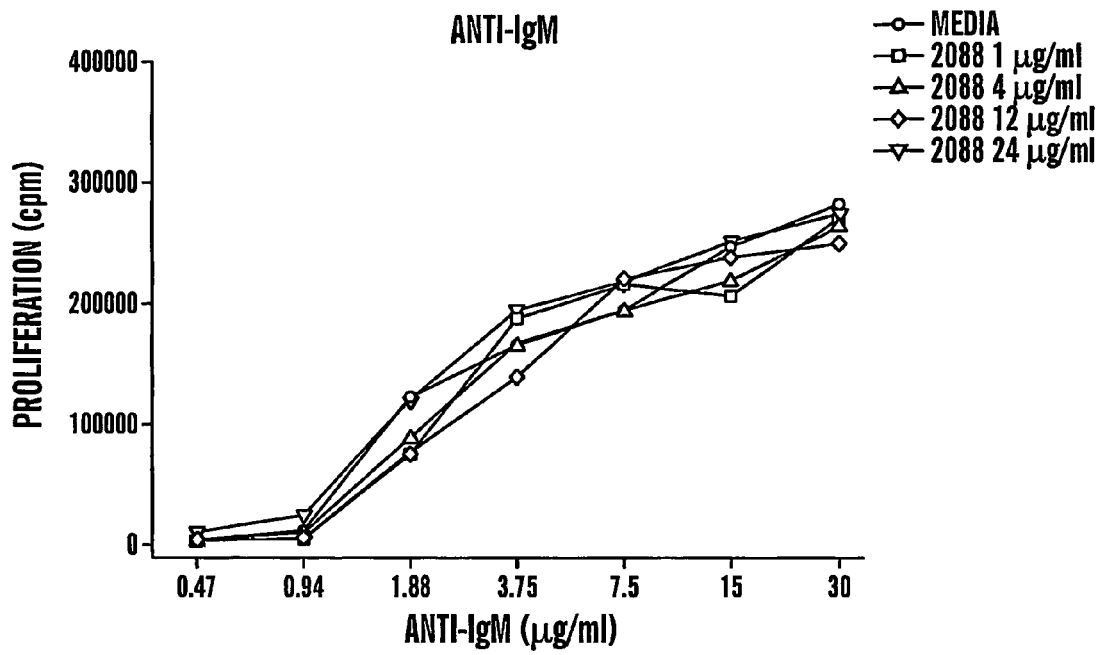
FIGS. 7A-7B show that B cells can be activated through TLR9 and that this activation can be blocked by TLR9 inhibition with ODN 2088. B cells were purified from the spleen of MRL+/+ mice and either pre-incubated, or not pre-incubated, for 30 minutes with varying doses of ODN 2088, an inhibitory oligodeoxynucleotide that specifically blocks signaling through TLR9. Anti-IgM F(ab')$_2$ (Anti-IgM), that activates through the B cell receptor (7A), or the stimulatory ODN 1826, that specifically activates through TLR9 (7B), was then added to the cultures. After 20-24 hours, $^3$[H] thymidine was added to the cultures and, after an additional 14-18 hours, proliferation was determined by measuring thymidine incorporation using an LKB Wallac 1212 Rackbeta counter. Only stimulation through TLR9 is blocked by ODN 2088 demonstrating the specificity of the inhibitory effect: stimulation induced by B cell receptor cross-linking is not inhibited.
Figure 7B:
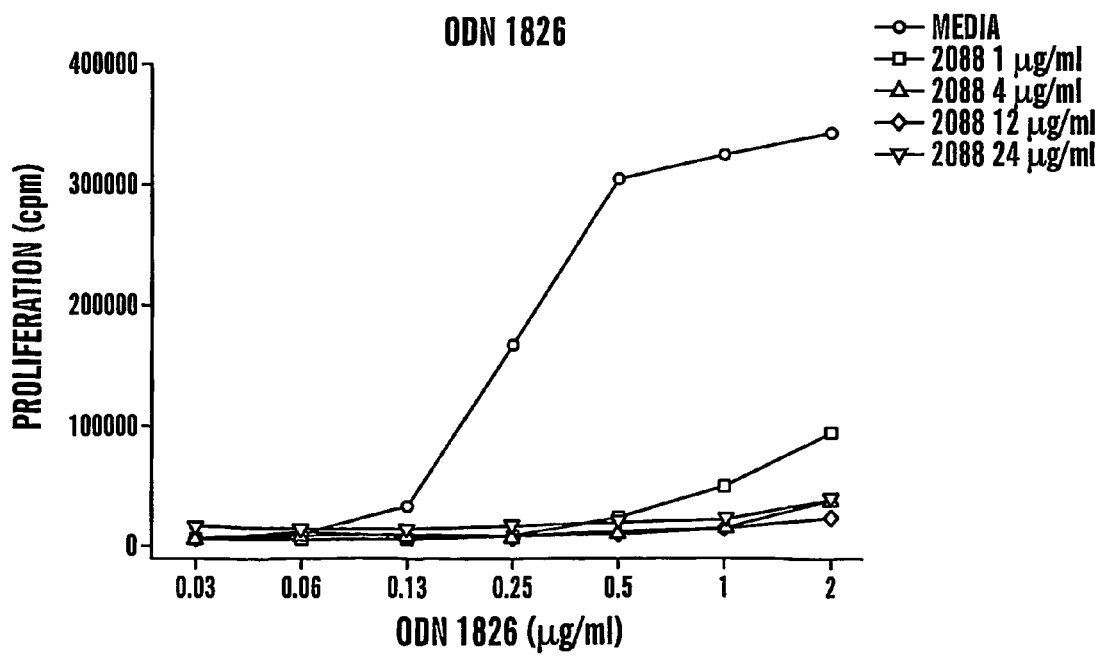

The B cell response to the stimulatory CpG S-ODN 1826 can also be blocked by a group of closely related inhibitory CpG S-ODN such as S-ODN 2088 (Lenart, et al., *Antisense Nucleic Acid Drug Dev.* 4, 247-256 (2001)). We found that S-ODN 2088 profoundly inhibited the proliferative response to S-ODN 1826 but had no effect on the response to anti-IgM or our TLR2 and TLR4 ligands (FIG. 5C and 5B). Most significantly, S-ODN 2088 also dramatically blocked the RF+ B cell response to mAb PL2-3. Overall, these data strongly implicate endosomal processing and/or engagement of an endosome-associated TLR, most probably TLR9, in RF+ B cell activation.

It has been clearly shown that autoreactive B cell clones can undergo isotype switching and somatic mutation, similar to the T-dependent features of conventional B cell responses to foreign antigens (Shlomchik, et al., *Nature* 328, 805-811 (1987)). However, more recent reports have suggested that autoreactive B cells may segregate from conventional B cells in the peripheral lymphoid tissues; autoreactive B cells tend to localize in the marginal zone of the splenic white pulp[26]pulp (Zeng, et al., *J. Immunol.* 164, 5000-5004 (2000)), while conventional B cells home to the follicular regions. In addition, in some instances, expansion and somatic mutation of autoreactive B cells can take place outside of the germinal center. These discrete localization patterns may reflect the preferential accumulation of stimulatory autoantibody/autoantigen IC at these sites. Alternatively, the relatively unique homing pattern may result from distinct chemokine receptor profiles elicited in response to the combined effects of BCR/TLR engagement. Future studies will need to compare the functional properties of B cells activated through BCR crosslinking alone from B cells activated through BCR/TLR dual engagement.

Autoantibodies that recognize DNA/nucleosomes are the defining and most prevalent specificity in SLE patients and murine lupus models of SLE, while RFs are characteristic of a subset of SLE patients, autoimmune-prone lpr mice, and RA patients. Remarkably, these same autoantigens are the targets in a number of new murine autoimmunity models generated by mutations that disrupt lymphocyte homeostasis or autoantigen metabolism (Botto, et al., *Nature Genetics* 19, 56-59 (1998); Bickerstaff, et al., *Nature Medicine* 5, 694-697 (1999); Napirei, et al., *Nat. Gen.* 25, 177-180 (2000); Scott, et al., *Nature* 411, 207-211 (2001)). The reason for the predominance of these particular specificities has been long-sought. Our data provide an explanation, namely the potent synergistic interaction of BCR/TLR signaling events mediated by chromatin containing immune complexes. In our experimental system, dependent on endosome/lysosome-localized TLR9 (Hacker, et al., *EMBO J.* 17, 6230-6240 (1998)), it is reasonable to conclude that autoantibody/autoantigen IC engagement of the BCR triggers the endocytosis of IC-associated antigen that then results in the highly efficient delivery of chromatin fragments to endosome-associated TLR9. In contrast to published studies (Bell, et al., *J. Clin. Invest.* 85, 1487-1496 (1990); Bell, et al., *Clin. Immunol. Immunopath.* 60, 1326 (1991)), we have been unable to activate B cells with either culture supernatants or chromatin fragments alone. Whether other strains of mice will prove more responsive to our fragments remains to be determined.

Beyond the current experimental model, the principle of BCR/TLR dual-engagement has wide ranging implications for autoimmunity in general. Model ligands such as haptenated-LPS and haptenated LPSLPS-coupled SRBC can also co-signal BCRs and TLRs and are remarkably potent and specific for the B cells that have the relevant receptors (Pike, *Methods Enzymol.* 1987;150:265-75, 1987). Activation in this mode is therefore likely to be a fundamental event in the loss of peripheral B cell tolerance in a wide variety of settings; other autoantigens may signal through TLRs other than TLR9. Overall, the data establish a critical role for endogenous TLR ligands in the aberrant activation of the adaptive immune system in autoimmunity and explain why the autoantibody repertoire is often skewed toward the recognition of subcellular nucleic acid/protein particles (Tan, E. *Adv. Immunol.* 44, 93-151 (1989)).

Methods

Mice. The MRL+/+ AM14 BCR Tg mice described previously (Hannum, et al., *J. Exp. Med.* 184, 1269-1278 (1996); Rifkin, et al., *J. Immunol.* 165, 1626-1633 (2000)) were crossed to Cr2-deficient mice, kindly provided by Dr. Michael Carroll (Harvard Medical School, Boston), and the F1 offsping were intercrossed to generate AM14 Cr2 deficient and Cr2 sufficient control mice. MyD88−/− mice, originally produced by Dr. Shizuo Akira (Osaka University, Osaka, Japan) (Adachi, et al., *Immunity* 9, 143-150 (1998)) and kindly provided through Dr. Douglas Golenbock (University of Massachusetts Medical School, Worcester, Mass.) were crossed to AM14 MRL+/+ mice to generate AM14 MyD88−/− and control littermate offspring. The RF+ offspring were initially identified by PCR, and their identity was confirmed by flow cytometric analysis of peripheral blood lymphocytes or spleen cells, using the 4-G7 monoclonal anti-idiotype as described (Shlomchik, et al., *Int. Immunol.* 5, 1329-1341 (1993)). Complement receptor genotype was determined by flow cytometry using the FITC-conjugated 7G6 antibody (Pharmingen, San Diego, Calif.). MyD88 genotype was determined by PCR using the primers: MyD88F (5'-TGG CAT GCC TCC ATC ATA GTT AAC C-3') [SEQ ID NO: 1], MyD88R (5'-GTC AGA AAC AAC CAC CAC CAT GC-3') [SEQ ID NO: 2], and neoR (5'-ATC GCC TTC TAT CGC CTT CTT GAC G-3') [SEQ ID NO: 3] (MWG Biotech, High Point, N.C.) to yield wild type and knockout products of approximately 550 bp and 750 bp respectively.

Cell culture and reagents. Spleen cell preparations were T-depleted and cultured with the appropriate ligands for 40-48 hrs. In some experiments, B cells were preincubated with CD40L as described (Rifkin, et al., *J. Immunol.* 165, 1626-1633 (2000)). Proliferation was assessed by $^3[H]$-thymidine incorporation during the final 16 hours of culture. Data are presented as the mean percentage of the anti-IgM response from triplicate cultures. The percentage of the anti-IgM response was calculated according to the formula: [(cpm experimental condition−cpm CD40L alone)/(cpm anti-IgM−cpm CD40L alone)×100].

Ligands included: goat anti-mouse IgM F(ab')$_2$ (15 µg/ml, Jackson ImmunoResearch Laboratories, West Grove, Pa.); the nucleosome specific mAbs PR1-3 (IgG2a$^j$), PL2-3 (IgG2a$^j$), and PL2-8 (IgG2b) (all at 50 µg/ml), kindly provided by Dr. Marc Monestier (Temple University School of Medicine, Philadelphia, Pa.) (Monestier and Novick *Mol. Immunol.* 33, 89-99 (1996)); 10 µg/ml LPS (Sigma, St. Louis, Mo.); 0.3-2 µg/ml stimulatory CpG S-ODN 1826 (Yi, et al., *J. Immunol.* 160, 4755-4761 (1998)) (Oligo's Etc, Wilsonville, Ohio), 10 µg/ml *Neisseria meningitidis* porin B (kindly provided by Dr. Lee Wetzler, Boston University School of Medicine, Boston, Mass.); 10 µg/ml synthetic lipopeptide Pam$_3$Cys-S$_4$ (Dr. G. Jung, Univ. of Tuebingen, Germany, kindly provided by Dr. Doug Golenbock); and the anti-TNP mAbs Hy1.2 (IgG2a$^a$) and C1040 (IgG2a$^b$) (Hannum, et al., *J. Exp. Med.* 184, 1269-1278 (1996)) (both at 50 µg/ml) complexed to varying concentrations of TNP-BSA. In some experiments, DNase I (type IV) (Sigma, St. Louis, Mo.), chloroquine (Sigma), concanamycin B, bafilomycin A (Sigma), or 12 µg/ml of the inhibitory CpG S-ODN 2008 (Lenart, et al., *Antisense Nucleic Acid Drug Dev.* 4, 247-256 (2001)) (Oligo's Etc.) were added to the cultures 15-30 min-2 hr before the addition of the ligands. All mAb and ODN preparations were shown to be endotoxin free by Limulus Amebocyte Lysate ELISA (Bio-Whittaker, Walkersville, Md.).

EXAMPLE 3

We have further shown that dendritic cells are activated by chromatin-containing immune complexes through sequential engagement of the Fc-receptor and TLR 9. This is a similar mechanism to that we have described for B cells except that in the case of the B cell, the relevant cell surface receptor is the B cell antigen receptor, whereas in dendritic cells the relevant cell surface receptor is an Fc gamma receptor (FcγR). Both cell surface receptors serve to deliver chromatin to TLR9 located within the endosome/lysosome compartment.

Figure 8A:
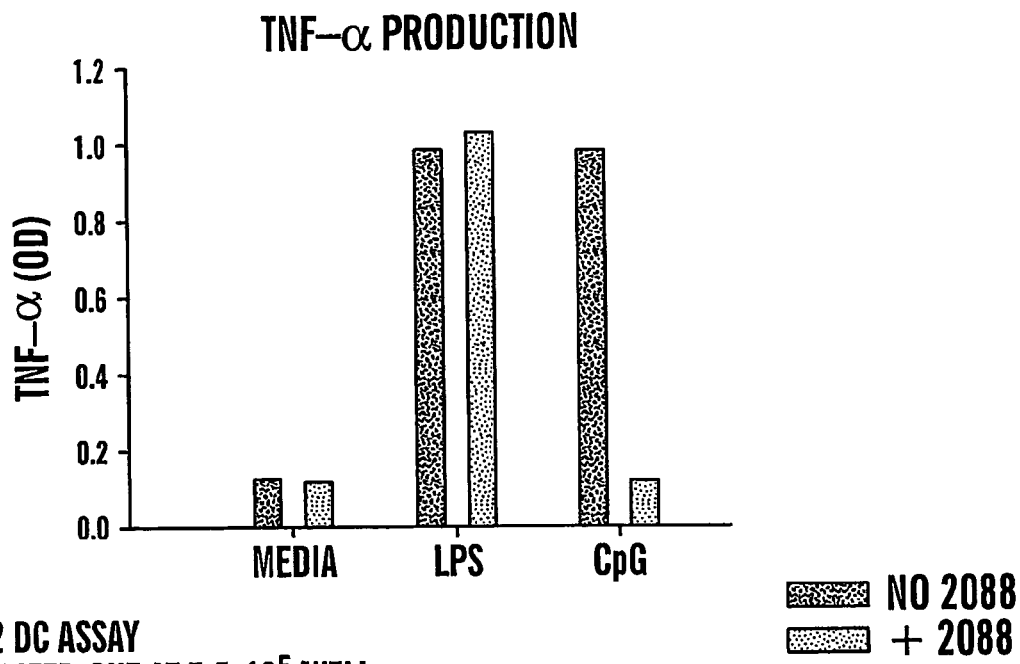
FIGS. 8A-8C show that dendritic cells can be specifically activated through TLR9 and this activation can be blocked by TLR9 inhibition with ODN 2088.
Figure 8B:
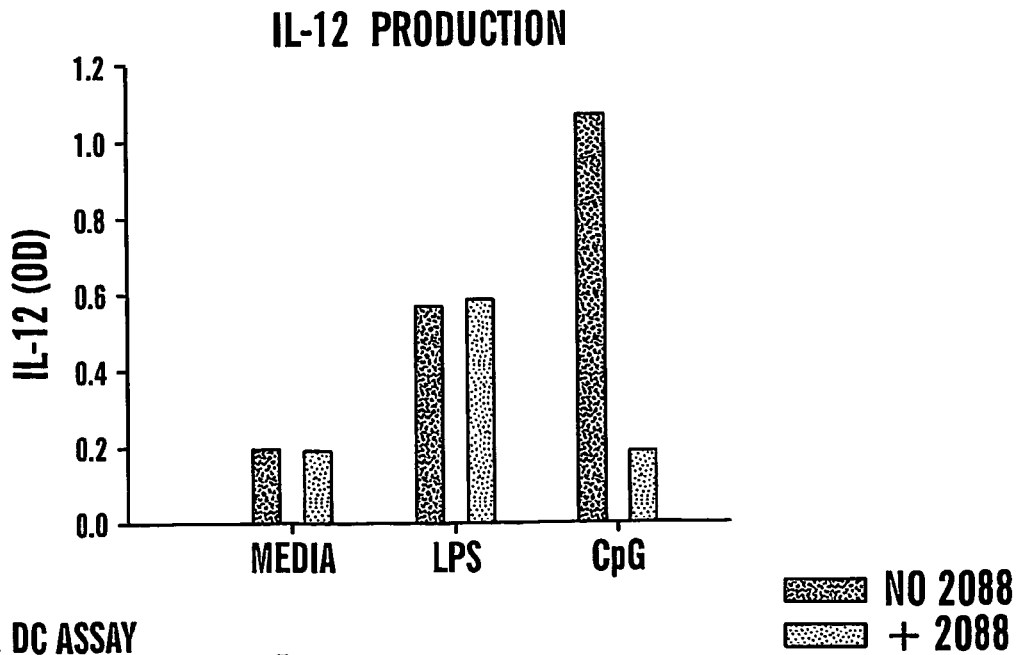
Figure 8C:
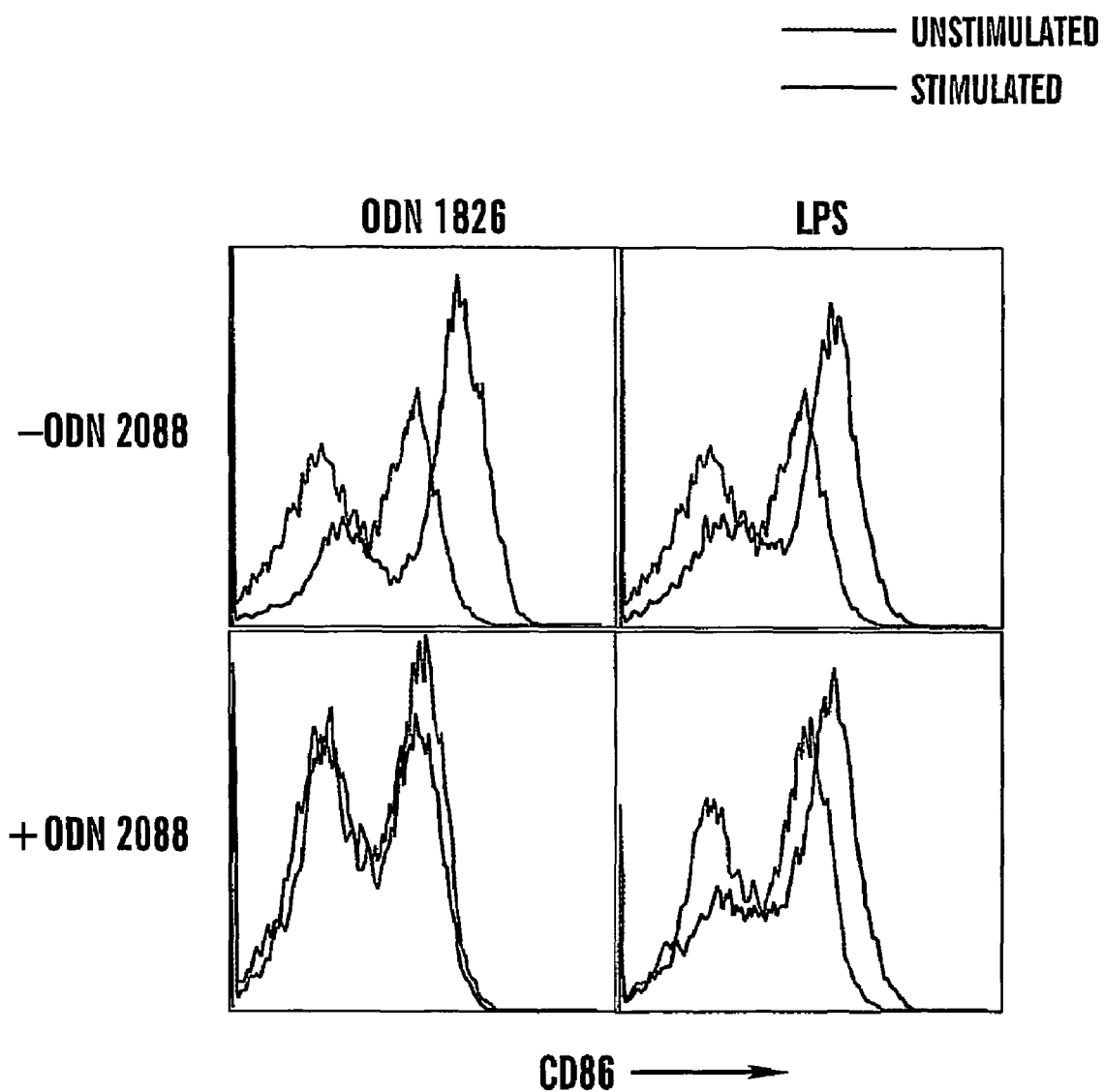
Figure 9:
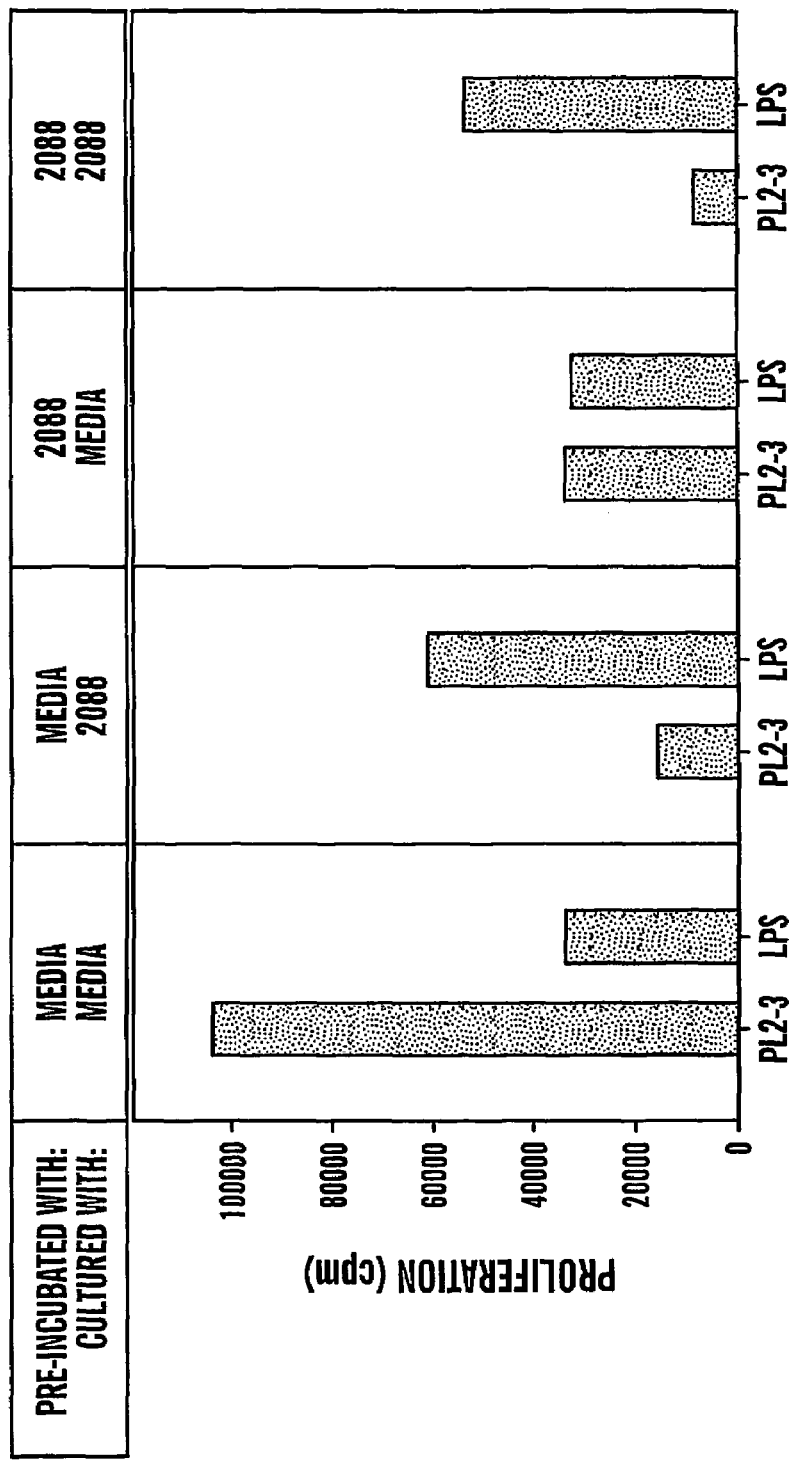
FIG. 9 shows the inhibitory effects of ODN 2088 on chromatin-containing immune complex mediated B cell proliferation are long-lasting. B cells were purified from the spleen of MRL+/+ mice and either pre-incubated, or not pre-incubated, for 16-20 hours with 12 µg/ml ODN 2088. After this pre-incubation, the cells were washed to remove ODN 2088 from the cultures and then the B cells were cultured with either medium alone or with fresh ODN 2088 at 12 µg/ml. Thirty minutes later the anti-chromatin monoclonal antibody PL2-3 (50 µg/ml) or LPS (10 µg/ml) were added to the cultures. After 20-24 hours, $^3$[H] thymidine was added to the cultures and, after an additional 14-18 hours, proliferation was determined by measuring thymidine incorporation using an LKB Wallac 1212 Rackbeta counter.

In FIGS. 8A-8C we show that dendritic cells can be specifically activated through TLR9 and this activation can be blocked by TLR9 inhibition with ODN 2088. These experiments demonstrate that the dendritic cells that we use in the subsequent experiments (shown in Tables 1 and 2 below) express functional TLR9, in that the specific TLR9 activating ligand ODN 1826 induces TNF-α and IL-12 production by the dendritic cells (8A, 8B) and furthermore induces upregulation of co-stimulatory molecules (8C). ODN 2088 is a specific inhibitor of the TLR9 mediated activation because (as shown in 8A, 8B, 8C), ODN 2088 blocks ODN 1826 mediated activation but has no effect on LPS mediated activation.

Dendritic cells were generated from the bone marrow of C57BL/6 mice by in vitro culture with GM-CSF and IL-4 for 6 days. On day 6, the CD11c positive dendritic cells were isolated using magnetic beads (Miltenyi Biotec) and either pre-incubated, or not pre-incubated, for 30 minutes with ODN 2088, an inhibitory oligodeoxynucleotide that specifically blocks signaling through TLR9. The stimulatory ODN 1826 (CpG, 3 µg/ml), that specifically activates through TLR9, or lipopolysaccharide (LPS, 10 µg/ml), that activates through TLR4, or culture medium only (media), was then added to the cultures. After 48 hours, levels of TNF-α (8A) and IL-12 (8B) in the culture supernatants were measured by ELISA (results shown as OD units determined by absorption at 405 nm). After removal of the supernatants, cells were collected and analyzed by flow cytometry for expression of the co-stimulatory molecule CD86 (8c). Unstimulated refers to the level of expression of CD86 in the presence of media alone, whereas stimulated refers to the level of expression of CD86 in the presence of the stimulus (ODN 1826 or LPS).

Table 1 below shows that chromatin-containing immune complexes (containing autoantibody in a complex with the chromatin autoantigen) activate dendritic cells to produce TNF-α whereas immune complexes containing a foreign antigen (TNP-BSA) do not induce this dendritic cell activation. Additionally, the activation induced by the chromatin-containing immune complexes is completely blocked by the TLR9 specific inhibitor ODN 2088, indicating that engagement of TLR9 (presumably by the chromatin within the chromatin-containing immune complex) is an essential component of the activation process.

TABLE 1

| Stimulus | None | 2088 |
|---|---|---|
| Media (no stimulus) | <50 | <50 |
| ODN 1826 | 2347 | <50 |
| LPS | 2514 | 2393 |
| PL2-3 | 1653 | <50 |
| TNP/αTNP-BSA IC 1:1 | <50 | <50 |
| TNP/αTNP-BSA IC 4:1 | <50 | <50 |
| TNP/αTNP-BSA IC 16:1 | <50 | <50 |

Table 1 shows that dendritic cell TNF-α production induced by chromatin-containing immune complexes is blocked by the TLR9 specific inhibitor ODN 2088. Dendritic cells were generated from the bone marrow of C57BL/6 mice by in vitro culture with GM-CSF and IL-4 for 6 days. On day 6, the CD11c positive dendritic cells were isolated using magnetic beads (Miltenyi Biotec). The dendritic cells were then either pre-incubated, or not pre-incubated, for 30 minutes with ODN 2088 at 12 µg/ml. The stimulatory ODN 1826 (3 µg/ml), that specifically activates through TLR9, lipopolysaccharide (LPS, 10 µg/ml), that activates through TLR4, the anti-chromatin antibody PL2-3 (50 µg/ml), three different antibody/protein ratios of α-TNP/TNP-BSA immune complexes (50 µg/ml), or the culture medium only (media), was then added to the cultures. After 48 hours, levels of TNF-α in the culture supernatants was measured by ELISA (results shown as pg/ml; lower level of sensitivity of assay is 50 pg/ml). A representative experiment of 3 similar experiments is shown.

Table 2 shows that chromatin-containing immune complexes induce TNF-α production by dendritic cells from wildtype mice (as was also seen in the studies shown in table 1 in the absence of ODN 2088) but completely fail to induce TNF-α production by dendritic cells from Fc receptor γ chain deficient mice. This demonstrates that an activating Fc receptor is absolutely required for dendritic cell activation by chromatin-containing immune complexes.

TABLE 2

| Stimulus | wildtype | Fc receptor γ chain deficient |
| --- | --- | --- |
| Media (no stimulus) | <50 | <50 |
| ODN 1826 | 7899 | 2373 |
| LPS | 7056 | 3411 |
| PL2-3 | 4554 | <50 |
| PL2-8 | 3964 | <50 |
| TNP/αTNP-BSA IC 1:1 | <50 | <50 |
| TNP/αTNP-BSA IC 4:1 | <50 | <50 |

Table 2 demonstrates that chromatin-containing immune complexes induce TNF-α production by dendritic cells from wildtype mice but do not induce TNF-α production by dendritic cells from Fc receptor γ chain deficient mice. Dendritic cells were generated from the bone marrow of C57BL/6 wildtype mice and from C57BL/6 mice lacking the Fc receptor γ chain in by in vitro culture of the bone marrow cells with GM-CSF and IL-4 for 6 days. On day 6, the CD11c positive dendritic cells were isolated using magnetic beads. The stimulatory ODN 1826 (3 µg/ml), that specifically activates through TLR9, lipopolysaccharide (LPS, 10 µg/ml), the anti-chromatin antibodies PL2-3 (50 µg/ml; IgG2a) and PL2-8 (50 µg/ml; IgG2b), two different antibody/protein ratios of α-TNP/TNP-BSA immune complexes (50 µg/ml), or the culture medium only (media), was then added to the dendritic cell cultures. After 48 hours, levels of TNF-α in the culture supernatants was measured by ELISA (results shown as pg/ml; lower level of sensitivity of assay is 50 pg/ml). A representative experiment of 2 similar experiments is shown.

Taken together, the data shown in Table 1 and Table 2 above demonstrate that dendritic cell activation induced by chromatin-containing immune complexes requires a signal through an activating Fcγ receptor as well as a signal mediated through TLR9.

Additional experiments to evaluate mechanisms and consequences of this FcγR/TLR dual engagement pathway are outlined below.

Characterization of the IFN-α Producing Dendritic Cell Subsets.

Mouse strains. Differences in dendritic cell and macrophage function between autoimmune lupus-like and non-autoimmune mouse strains have been described. These include differences in immune complex handling (Jones et al., Clin. Immunol. Immunopathol. 36: 30-39, 1985; Magilavy et al., J. Immunol. 131: 2784-2788, 1983), phagocytosis (Russell, and Steinberg Clin. Immunol. Immunopathol. 27: 387-402, 1983), Fc receptor expression and function (Pritchard et al., Current Biology. 10: 227-230, 2000; Jiang et al., Immunogenetics. 51: 429-435., 2000) and cytokine production (Allevae et al., J. Immunol. 159: 5610-5619., 1997; Kohet al., J. Immunol. 165: 4190-4201., 2000). It is therefore important to directly compare dendritic cells derived from both autoimmune and non-autoimmune strains. MRL+/+ and (NZB× NZW) F1 are the two autoimmune lupus-like strains and C57BL/6 and BALB/c are the two non-autoimmune strains that are used.

Purification of dendritic cell subsets. There are 2 dendritic cell subsets which are particularly important in the pathogenesis of SLE: CD11c+ CD8α+ and CD11c+ B220+ Gr-1+. These cells are either obtained directly from the spleen (Hochrein et al., J. Immunol. 166: 5448-5455, 2000; Nakano et al., J. Exp. Med. 194: 1171-1178, 2001) or generated by in vitro culture of bone marrow cells in the presence of Flt3 ligand (Brasel et al., Blood. 96: 3029-3039, 2000; Gilliet et al., J. Exp. Med. 195: 953-958, 2002). Splenic dendritic cells are isolated as described (Vremec et al., J. Immunol. 164: 2978-2986, 2000) and, after appropriate fluorescent antibody staining, the specific dendritic cell subsets are fractionated and collected using a MoFlo cell sorter (Cytomation, Fort Collins, Colo.). The CD11c+ CD8α-dendritic cell subset, which is also found in the spleen, are isolated at the same time as the target CD11c+ CD8α+ dendritic cell subset and used as an experimental control.

To generate bone marrow derived dendritic cells, bone marrow cells are harvested and cultured in vitro for 6-10 days in the presence of recombinant murine Flt3 ligand using established protocols (Gilliet et al., J. Exp. Med. 195: 953-958, 2002; Labeur et al., J. Immunol. 162: 168-175, 1999). Bone marrow cells grown in Flt3 ligand are enriched in the target populations, namely CD11c+ CD8+ and CD11c+ B220+ Gr-1+ dendritic cells. These populations are fractionated by cell sorting as described above for the spleen-derived dendritic cells.

Determining the expression of TLR9 in the specific dendritic cell subsets. TLR9 messenger RNA is measured by quantitative reverse transcription polymerase chain reaction (RT-PCR). In addition, the response of the dendritic cell subsets to a TLR9-specific stimulatory ligand, S-ODN 1826 (Ballas et al., J. Immunol. 167: 4878-4886, 2001), are compared by measuring expression of co-stimulatory molecules and cytokine production. Specific antibodies against murine TLR9 can be produced using techniques known to one skilled in the art.

Preparation of IC and Assessment of IC Binding and Uptake by Dendritic Cells.

Immune complex preparation. Anti-nucleosome/chromatin IC is prepared by incubating the anti-nucleosome monoclonal antibodies PL2-3 (IgG2a), PL2-8 (IgG2b) and PL9-7 (IgG3) with supernatant obtained from 24 hour in vitro cultures of spleen cells. Chromatin is spontaneously released from spleen cells in culture (Bell et al., J. Clin. Invest. 85: 1487-1496, 1990) and binding of the anti-nucleosome antibodies to this chromatin results in the formation of IC which can be measured using a C1q immunoassay (Rifkin et al., Journal of Immunology. 165: 1626-1633, 2000). We have further shown that biotinylated PL2-3 preincubated with culture fluid binds specifically to rheumatoid factor B cells as detected by flow cytometry; monomeric biotinylated PL2-3 does not bind. Non-self antigen control IC is made using the anti-TNP monoclonal antibodies Hy1.2 (IgG2a) or C4010 (IgG2b) and incubating them with TNP-BSA, with confirmation of IC formation also by C1q binding as demonstrated (Leadbetter et al., Nature. 416: 603-607, 2002). Additional non-self antigen control IC is made using the anti-ovalbumin monoclonal antibodies Ov1 (IgG2a) and Ov2 (IgG2b) prepared in this laboratory and incubating them with ovalbumin. As well as demonstrating IC formation in a C1q binding assay, FPLC is also used as an additional confirmatory assay.

Immune complex binding and uptake by dendritic cells. Before setting up the actual experimental cultures containing the IC and dendritic cells, it is necessary to determine the extent to which the purified dendritic cell subsets from the different strains are able to bind and take up IC. This is particularly important given the reported differences between autoimmune and non-autoimmune mouse strains as regards IC handling (Jones et al., Clin. Immunol. Immunopathol. 36: 30-39, 1985; Magilavy et al., J. Immunol. 131: 2784-2788, 1983) and Fc receptor expression (Pritchard et al., Current Biology. 10: 227-230, 2000; Jiang et al., Immunogenetics. 51: 429-435., 2000). The experimental approach is to track the antibody component of the immune complex using a combination of flow cytometry and confocal microscopy. The anti-nucleosome antibodies PL2-3 (IgG2a), PL2-8 (IgG2b) and PL9-7 (IgG3) are biotin-conjugated, using standard procedures, and biotin-anti-nucleosome/chromatin IC are prepared as above. To confirm that the biotin-anti-nucleosome/chromatin IC retains functionality it is assessed whether the biotin-PL2-3/chromatin IC is able to induce proliferation in rheumatoid factor B cells to the same extent as the non-biotin-PL2-3/chromatin IC (Rifkin et al., Journal of Immunology. 165: 1626-1633, 2000). The biotin-PL2-8/chromatin IC and the biotin-PL9-7/chromatin IC cannot be tested in this way because IgG2b and IgG3 are not recognized by the rheumatoid factor B cell receptor, but it is assumed that the functional effect of biotin-conjugation will be similar irrespective of isotype. Isotype-matched biotin-anti-TNP/TNP-BSA IC and biotin-anti-ovalbumin/ovalbumin IC are prepared similarly. Biotin-conjugated antibodies alone not made into complexes are used as controls. The biotin-conjugated IC and biotin-conjugated antibodies alone are added to the different dendritic cell subsets, and flow cytometry is used to detect cell surface binding. The biotin-labeled compounds are visualized with an anti-biotin monoclonal antibody conjugated to a specific fluorochrome (Molecular Probes: anti-biotin mouse monoclonal 2F5 Alexa Fluor 488 conjugate). Subsequently, confocal microscopy is used to assess dendritic cell internalization of the anti-nucleosome antibody (biotin-anti-nucleosome/chromatin IC), the anti-TNP antibody (biotin-anti-TNP/TNP-BSA IC) or the anti-ovalbumin antibody (biotin-anti-ovalbumin/ovalbumin IC) following incubation periods of 1-12 hours and fixation with 3% paraformaldehyde.

In addition, co-localization studies are performed by co-staining with fluorescent-labeled monoclonal antibodies specific for endosomal/lysosomal compartments, or by the use of fluorescent pH indicators that partition into acidic organelles (Molecular Probes).

Measurement of Dendritic Cell Activation by Chromatin-Containing IC and Establishment of the Role of Toll-Like Receptors and Fc Gamma Receptors.

Measuring dendritic cell activation by IC. The anti-nucleosome/chromatin IC, anti-TNP/TNP-BSA IC and anti-ovalbumin/ovalbumin IC outlined above are incubated with the dendritic cell subsets and dendritic cell activation determined by measuring upregulation of co-stimulatory molecules and cytokine production. Controls include the monomeric non-complexed antibodies alone, antigens alone, stimulatory CpG S-ODN 1826 as a positive control for TLR9 signaling, LPS as a positive control for TLR4 signaling and porin B as a positive control for TLR2 signaling. Cytokines are measured by ELISA and include IL-12, TNF-$\alpha$, IL-10 and IFN-$\alpha$. IL-12 and TNF-$\alpha$ are the two cytokines most commonly used as markers of dendritic cell activation (Banchereau et al., Annu. Rev. Immunol. 18: 767-811, 2000) and IFN-$\alpha$ is the cytokine most strongly associated with the activation of the CD11c+ CD8$\alpha$+ and the CD11c+ B220+ Gr-1+ dendritic cell subsets. It is necessary to measure IL-10 as it has been shown that Fc receptor engagement in macrophages can lead to IL-10 production induced by a subsequent stimulus which, in the absence of Fc receptor engagement, leads to IL-12 and not IL-10 production (Gerber and Mosser J. Immunol. 166: 6861-6868., 2001). The increased expression of MHC class II and the co-stimulatory molecules CD80, CD86, and CD40 is determined by flow cytometry.

Role of Toll-like receptors and Fc gamma receptors in IC-mediated dendritic cell activation S-ODN 2088 is an inhibitory CpG S-ODN which specifically blocks signaling through TLR9 (Lenert et al., Antisense and Nucleic Acid Drug Development 11: 247-256, 2001). We have shown that S-ODN 2088 strongly inhibits the chromatin-containing IC-induced proliferation of B cells from rheumatoid factor B cell receptor transgenic mice (Leadbetter et al., Nature. 416: 603-607, 2002 (Leadbetter et al., Nature. 416: 603-607, 2002). Also, we have shown that S-ODN 2088 completely prevents dendritic cell activation by stimulatory CpG S-ODN (such as S-ODN 1826) acting through TLR9. The experiments outlined above are done in the presence or absence of S-ODN 2088 to assess the role of TLR9 in IC-mediated dendritic cell activation. They are also done in the presence and absence of inhibitors of endosomal acidification, including chloroquine, concanamycin B and bafilomycin A, which prevent signaling through TLR9. In addition, dendritic cells from C57BL/6 MyD88+/+ mice are compared to dendritic cells from C57BL/6 MyD88–/– mice to establish the requirement for TLR signaling.

In order to assess the requirement for Fc gamma receptor (Fc$\gamma$R) signaling, experiments are also done in the presence and absence of 2.4.G2, a monoclonal antibody that specifically blocks murine Fc$\gamma$RII and Fc$\gamma$RIII (Araujo-Jorge et al., Infect Immun. 61: 4925-4928., 1993). However, the third type of murine Fc gamma receptor, Fc$\gamma$R I, is not blocked by 2.4G2 and can mediate IC-induced inflammatory responses (Ioan-Facsinay et al., Immunity. 16: 391-402., 2002; Barnes et al., Immunity. 16: 379-389, 2002). Dendritic cells express all three classes of Fc$\gamma$R (Fc$\gamma$RI, Fc$\gamma$RII and Fc$\gamma$RIII) (Ravetch and Bolland, Ann. Rev. Immunol. 19: 275-290, 2001). Therefore, additional studies can be performed using Fc$\gamma$R knockout mice. The mice are available from Jackson Laboratories, and include i) mice rendered genetically deficient in Fc$\gamma$RI and Fc$\gamma$RIII by knockout of the common stimulatory signal-transducing gamma chain shared by these two receptors (Takai et al., Cell. 76: 519-529., 1994) ii) Fc$\gamma$RII knockout mice (Takai et al., Nature. 379: 346-349., 1996) and iii) Fc$\gamma$RIII knockout mice (Hazenbos et al., Immunity. 5: 181-188., 1996).

Role of IC and TLR9 in antigen processing and presentation by dendritic cells. CD4+ autoreactive T cells are central to the pathogenesis of SLE, both in humans and in murine models of the disease (Craft et al., Immunol. Res. 19:, 1999; Hoffman, Front. Biosci. 6: D1369-78, 2001; Shlomchik et al., Nature Rev. Immunol. 1: 147-153., 2001). Dendritic cells are the key antigen presenting cells involved in initiating T cell responses (Banchereau et al., Annu. Rev. Immunol. 18: 767-811, 2000) and TLR9 engagement has been shown to strongly promote development of Th1-type immune responses (Jakob et al., J. Immunol. 161: 3042-3049, 1998; Lipford et al., J. Immunol. 165: 1228-1235., 2000). To show whether TLR9 engagement alters the T cell response to antigen contained within immune complexes, ovalbumin is conjugated to the stimulatory CpG S-ODN 1826 as described (Shirota et al., J. Immunol. 164: 5575-5582., 2000). IC is consequently made by incubating unconjugated ovalbumin or the ovalbumin-CpG conjugate with the anti-ovalbumin monoclonal antibodies Ov1 (IgG2a) or Ov2 (IgG2b). Dendritic cell subsets from BALB/c mice (H-$2^d$) are pulsed with these IC. CD4+ T cells, which recognize ovalbumin in the context of H-$2A^d$, are purified from the lymph nodes of ovalbumin-specific T cell receptor transgenic mice (DO11.10 mice) (Murphy et al., Science. 250: 1720-1723, 1990). These CD4+ T cells are cultured with the IC-pulsed dendritic cells and T cell proliferation and cytokine production (IFN-gamma, IL-4 and IL-2) is measured during primary and secondary T cell responses. S-ODN 2088 and endosomal acidification inhibitors is used to assess the role of TLR9.

REFERENCES

1. Tan, E. *Adv. Immunol.* 44, 93-151 (1989).
2. Theofilopoulos, et al., *J. Exp. Med.* 162, 1-18 (1985).
3. Wolfowicz, et al., *Clin. Immunol. Immunopath.* 46, 382-395 (1988).
4. Shlomchik, et al., *Int. Immunol.* 5, 1329-1341 (1993).
5. Jacobson, et al., *J. Immunol.* 152, 4489-99 (1994).
6. Hannum, et al., *J. Exp. Med.* 184, 1269-1278 (1996).
7. Wang, and Shlomchik, *J. Exp. Med.* 190, 639-649 (1999).
8. Rifkin, et al., *J. Immunol.* 165, 1626-1633 (2000).
9. Emlen, et al., *J. Immunol.* 148, 3042-3048 (1992).
10. Monestier and Novick *Mol. Immunol.* 33, 89-99 (1996).
11. Carter et al., *J. Immunol.* 141, 457-463 (1988).
12. Ahearn, et al., *Immunity* 4, 251-262 (1996).
13. Lemaitre et al., *Cell* 86, 973-983 (1996).
14. Medzhitov, et al., *Nature* 388, 323-324 (1997).
15. Akira, et al., *Nat. Immunol.* 2, 675-680 (2001).
16. Li, et al., *J. Immunol.* 166, 7128-7135 (2001).
17. Horng, et al., *Nat. Immunol.* 2, 835-841 (2001).
18. Adachi, et al., *Immunity* 9, 143-150(1998).
19. Hacker, et al., *J. Exp. Med.* 192, 595-600 (2000).
20. Singal and Ginder *Blood* 93, 4059-4070 (1999).
21. Hemmi, et al., *Nature* 408, 740-745 (2000).
22. Yi, et al., *J. Immunol.* 160, 4755-4761 (1998).
23. Hacker, et al., *EMBO J.* 17, 6230-6240 (1998).
24. Benaroch, et al., *EMBO J.* 14, 37-49 (1995).
25. Massari, et al., *J. Immunol.* (in press).
26. Group, T. C. H. S. *N. Engl. J. Med.* 324, 150-154 (1991).
27. Furst, et al., *Arth. Rheu.* 42, 357-365 (1999).
28. Lenart, et al., *Antisense Nucleic Acid Drug Dev.* 4, 247-256 (2001).
29. Shlomchik, et al., *Nature* 328, 805-811 (1987).
30. Zeng, et al., *J. Immunol.* 164, 5000-5004 (2000).
31. Botto, et al., *Nature Genetics* 19, 56-59 (1998).
32. Bickerstaff, et al., *Nature Medicine* 5, 694-697 (1999).
33. Napirei, et al., *Nat. Gen.* 25, 177-180 (2000).
34. Scott, et al., *Nature* 411, 207-211 (2001).
35. Bell, et al., *J. Clin. Invest.* 85, 1487-1496 (1990).
36. Bell, et al., *Clin. Immunol. Immunopath.* 60, 1326 (1991).
37. Moller, et al., *Cell. Immunol.* 4, 416-424 (1972).
38. Blanco, et al., Science. 294: 1540-1543., 2001.
39. Vallin, et al., Clin. Exp. Immunol. 115: 196-202, 1999.
40. Vallin, et al., J. Immunol. 163: 6306-6313, 1999.
41. Cella, et al., Nat. Med. 5: 919-923., 1999.
42. Siegal, et al., Science. 284: 1835-1837., 1999.
43. Hooks, et al., N. Engl. J. Med. 301: 5-8., 1979.
44. Ytterberg, et al., Arthritis Rheum. 25: 401-406., 1982.
45. Bengtsson, et al., Lupus. 9: 664-671., 2000.

The references cited herein and throughout the specification are herein incorporated by reference in their entirety.

---

What is claimed is:

1. A method of treating a patient having systemic lupus erythematosus, comprising administering to a patient having systemic lupus erythematosus an effective amount of an inhibitory CpG S-ODN oligonucleotide that inhibits an immune complex or autoantigen from binding to or activating Toll-like receptor-9 (TLR9), wherein said immune complex comprises an autoantibody and an autoantigen bound to a cell receptor, to treat the systemic lupus erythematosus.

2. The method of claim 1, wherein the inhibitory CpG S-ODN oligonucleotide is ODN 2088.

* * * * *

UNITED STATES PATENT AND TRADEMARK OFFICE
CERTIFICATE OF CORRECTION

PATENT NO. : 7,709,451 B2  Page 1 of 1
APPLICATION NO. : 10/487885
DATED : May 4, 2010
INVENTOR(S) : Ann Marshak-Rothstein et al.

It is certified that error appears in the above-identified patent and that said Letters Patent is hereby corrected as shown below:

Title Page,

In the Related U.S. Application Data, field 60, lines 2-3, "provisional application No. 60/067,578, filed on Sep. 19, 1997." should read --provisional application No. 60/367,578, filed March 26, 2002.--

Signed and Sealed this

Twenty-eighth Day of September, 2010

David J. Kappos
*Director of the United States Patent and Trademark Office*